US010857230B2

(12) United States Patent
Quigley et al.

(10) Patent No.: US 10,857,230 B2
(45) Date of Patent: Dec. 8, 2020

(54) CO-THERAPY COMPRISING A SMALL MOLECULE CSF-1R INHIBITOR AND AN AGONISTIC ANTIBODY THAT SPECIFICALLY BINDS CD40 FOR THE TREATMENT OF CANCER

(71) Applicant: Janssen Biotech, Inc., Horsham, PA (US)

(72) Inventors: Michael Quigley, Ambler, PA (US); Andressa Smith, Lansdale, PA (US)

(73) Assignee: Janssen Biotech, Inc., Horsham, PA (US)

( * ) Notice: Subject to any disclaimer, the term of this patent is extended or adjusted under 35 U.S.C. 154(b) by 159 days.

(21) Appl. No.: 15/910,392

(22) Filed: Mar. 2, 2018

(65) Prior Publication Data

US 2018/0250398 A1 Sep. 6, 2018

Related U.S. Application Data

(60) Provisional application No. 62/500,313, filed on May 2, 2017, provisional application No. 62/466,503, filed on Mar. 3, 2017.

(51) Int. Cl.
| | |
|---|---|
| *A61K 39/00* | (2006.01) |
| *A61K 39/395* | (2006.01) |
| *A61K 31/4439* | (2006.01) |
| *A61P 35/00* | (2006.01) |
| *C07K 16/28* | (2006.01) |
| *C07K 16/30* | (2006.01) |
| *A61K 45/06* | (2006.01) |
| *A61K 31/501* | (2006.01) |

(52) U.S. Cl.
CPC .... *A61K 39/39558* (2013.01); *A61K 31/4439* (2013.01); *A61K 31/501* (2013.01); *A61K 39/395* (2013.01); *A61K 45/06* (2013.01); *A61P 35/00* (2018.01); *C07K 16/2866* (2013.01); *C07K 16/2878* (2013.01); *C07K 16/3046* (2013.01); *A61K 2039/505* (2013.01); *A61K 2039/507* (2013.01); *C07K 2317/30* (2013.01); *C07K 2317/56* (2013.01); *C07K 2317/565* (2013.01); *C07K 2317/75* (2013.01); *C07K 2317/76* (2013.01)

(58) Field of Classification Search
CPC .................................................. A61K 39/39558
See application file for complete search history.

(56) References Cited

U.S. PATENT DOCUMENTS

| | | | |
|---|---|---|---|
| 2004/0197332 A1 | 10/2004 | Ullrich et al. | |
| 2009/0105296 A1 | 4/2009 | Illig et al. | |
| 2014/0079706 A1 | 3/2014 | Cannarile et al. | |
| 2014/0179907 A1* | 6/2014 | Barrett ............... | C07K 16/2878 536/23.53 |
| 2014/0348836 A1 | 11/2014 | Ellmark et al. | |
| 2016/0016942 A1* | 1/2016 | Chen .................... | C07D 405/14 514/341 |
| 2017/0088624 A1* | 3/2017 | Fransson ............ | C07K 16/4208 |
| 2018/0085472 A1 | 3/2018 | Masteller et al. | |

FOREIGN PATENT DOCUMENTS

| | | | |
|---|---|---|---|
| WO | WO 88/01649 A1 | 3/1988 | |
| WO | WO 92/01047 A1 | 1/1992 | |
| WO | WO 94/13804 A1 | 6/1994 | |
| WO | WO 98/44001 A1 | 10/1998 | |
| WO | WO 2005/011734 A2 | 2/2005 | |
| WO | WO 2009/085462 A1 | 7/2009 | |
| WO | WO-2013034904 A1 * | 3/2013 | ............... A61K 9/20 |
| WO | WO 2013/132044 A1 | 9/2013 | |
| WO | WO-2016023960 A1 * | 2/2016 | ......... A61K 39/3955 |
| WO | WO-2016100882 A1 * | 6/2016 | ............ C07K 16/28 |
| WO | WO 2016/168149 A1 | 10/2016 | |
| WO | WO 2018/036852 A1 | 3/2018 | |

OTHER PUBLICATIONS

Beck, A.H., et al., "The Macrophage Colony-Stimulating Factor 1 Response Signature in Breast Carcinoma", (2009), Clin Cancer Res, vol. 15, No. 3, pp. 778-787.
Bingle, L., et al., "The role of tumour-associated macrophages in tumour progression: implications for new anticancer therapies", (2002), Journal of Pathology, vol. 196, No. 3, pp. 254-265.
Bourette, R.P., et al., "Early Events in M-CSF Receptor Signaling", (2000), Growth Factor 17, pp. 155-166.
Chothia, C., et al., "Canonical Structures for the Hypervariable Regions of Immunoglobulins", (1987), J. Mol. Biol.196, pp. 901-917.
Coussens, L., et al., "Structural alteration of viral homologue of receptor proto-oncogene fms at carboxyl terminus", (1986), Nature 320, pp. 277-280.
Dai, X., et al., "Targeted disruption of the mouse colony-stimulating factor 1 receptor gene results in osteopetrosis, mononuclear phagocyte deficiency, increased primitive progenitor cell frequencies, and reproductive defects", (2002), Blood 99, pp. 111-120.
Denardo, D.G., et al., "CD4+T Cells Regulatae Pulmonary Metastasis of Mamary Carcinomas by Enhancing Protumor Properties of Macrophages", (2009), Cancer Cell 16, pp. 91-102.
Denardo, D.G., et al., "Leukocyte Complexity Predicts Breast Cancer Survival and Functionally Regulates Response to Chemotherapy", (2011), Cancer Discovery 1, pp. 54-67.

(Continued)

*Primary Examiner* — Sheela J. Huff
(74) *Attorney, Agent, or Firm* — BakerHostetler

(57) ABSTRACT

The present invention is directed to methods for treating cancer, preferably a solid tumor or hematological malignancy, including for example pancreatic cancer, lung cancer (including but not limited to non-small cell lung cancer (NSCLC)), prostate cancer, colorectal cancer, breast cancer, melanoma or non-Hodgkin's lymphoma, comprising administering to a subject in need thereof a therapeutically effective amount of co-therapy comprising, consisting or consisting essentially of (a) a small molecule CSF-1R inhibitor and (b) an agonistic antibody that binds CD40.

47 Claims, No Drawings

Specification includes a Sequence Listing.

(56) References Cited

OTHER PUBLICATIONS

Espinosa, I., et al., "Coordinate Expression of Colony-Stimulating Factor-1 and Colony-Stimulating Factor-1-Related Proteins is Associated with Poor Prognosis in Gynecological and Nongynecological Leiomyosarcoma", (2009), Am. J. Pathol, vol. 174, No. 6, pp. 2347-2356.
French, R.R., et al., "CD40 antibody evokes a cytotoxic T-cell response that eradicates lymphoma and bypasses T-cell help", (1999), Nature Medicine, vol. 5, No. 5, pp. 548-553.
Freshney, R.I., "Culture of Animal Cells: A Manual of Basic Technique", (1994), Wiley-Liss, 3$^{rd}$ edition, Table of Contents.
Honegger, A., et al., "Yet Another Numbering Scheme for Immunoglobulin Variable Domains: An Automatic Modeling and Analysis Tool", (2001), J. Mol. Biol. 309, pp. 657-670.
Hume, D.A., et al., "Therapeutic applications of macrophage colony-stimulating factor-1 (CSF-1) and antagonists of CSF-1 receptor (CSF-1R) signaling", (2012), Blood, vol. 119, No. 8, pp. 1810-1820.
IMGT®, the international ImMunoGeneTics information system® web resources, http;//www.imgt.org, created in (1989).
Kawai, O., et al., "Predominant Infiltration of Macrophages and CD8$^+$T Cells in Cancer Nests is a Significant Predictor of Survival in Stage IV Nonsmall Cell Lung Cancer", (2008), Cancer, vol. 113, No. 6, pp. 1387-1395.
Kawamura, K., et al., "Detection of M2 macrophages and colony-stimulating factor 1 expression in serous and mucinous ovarian epithelial tumors", (2009), Pathology International 59, pp. 300-305.
Knappik, A., et al., "Fully Synthetic Human Combinatorial Antibody Libraries (HuCAL) Base on Modular Consensus Frameworks and CDRs Randomized with Trinucleotides", (2000), J. Mol. Biol. 296, pp. 57-86.
Lee, P.S.W., et al., "The Cbl protooncoprotein stimulates CSF-1 receptor multiibiquitination and endocytosis, and attenuates macrophage proliferation", (1999), The EMBO Journal, vol. 18, No. 13, pp. 3616-3628.
Lefranc, M., et al., "IMGT unique numbering for immunoglobulin and T cell receptor variable domains and Ig superfamily V-like domains", (2003), Dev Comp Immunol 27, pp. 55-77.
Li, W., et al., "Role of dimerization and modification of the CSF-1 receptor in its activation and internalization during the CSF-1 response", (1991), The EMBO Journal, vol. 10, No. 2, pp. 277-288.
Lin, H., et al., "Discovery of a Cytokine and Its Receptor by Functional Screening of the Extracellular Proteome", (2008), Science 320, pp. 807-811.
Lin, E.Y., et al., "Colony-stimulating Factor 1 Promotes Progression of Mammary Tumors to Malignancy", (2001), J. Exp. Med., vol. 193, No. 6, pp. 727-740.
Määttä, J.A., et al., "Proteolytic Cleavage and Phosphorylation of a Tumor-associated ErbB4 Isoform Promote Ligand-independent Survival and Cancer Cell Growth", (2006), Molecular Biology of the Cell 17, pp. 67-79.
Mantovani, A., et al., "Tumour-associated macrophages as a prototypic type II polarized phagocyte population: role in tumour progression", (2004), European Journal of Cancer 40, pp. 1660-1667.
Mantovani, A., et al., "Macrophages, innate immunity and cancer: balance, tolerance, and diversity", (2010), Current Opinion in Immunology 22, pp. 231-237.
Melief, C.J.M., et al., "Strategies for Immunotherapy of Cancer", (2000), Advances in Immunology 75, pp. 235-282.
Orre, M., et al., "Macrophages and Microvessel Density in Tumors of the Ovary", (1999), Gynecologic Oncology vol. 73, No. 1, pp. 47-50.
Pixley, F., et al., "CSF-1 regulation of the wandering macrophage: complexity in action", (2004), Trends in Cell Biology, vol. 14, No. 11, pp. 628-638.
Pollard, J.W., "Role of Colony-Stimulating Factor-1 in Reproduction and Development", (1997), Mol. Reprod. Dev. 46, pp. 54-61.
Remington: The Science and Practice of Pharmacy, 21$^{st}$ edition, Troy, D.B. editor, (2006), Part 5: Pharmaceutical Manufacturing, Lipincott Williams and Wilkins—Table of Contents.
Roth, P., et al., "The Biology of CSF-1 and Its Receptor", (1992), Current Topics in Microbiology 181, pp. 141-167.
Roussel, M.F., et al., "Transforming potential of the c-fms proto-oncogene (CSF-1 receptor)", (1987), Nature 325, pp. 549-552.
Sherr, C.J., et al., "The c-fms Proto-oncogene Product is Related to the Receptor for the Mononuclear Phagocyte Growth Factor, CSF-1", (1985), Cell 41, pp. 665-676.
Shi, L., et al., De Novo Selection of High-Affinity Antibodies from Synthetic Fab Libraries Displayed on Phage as pIX Fusion Proteins, (2010), J. Mol. Biol. 397, pp. 385-396.
Sotomayor, E.M., et al., "Conversion of tumor-specific CD4$^+$ T-cell tolerance to T-cell priming through in vivo ligation of CD40", (1999), Nature Medicine, vol. 5, No. 7, pp. 780-787.
Stanley, E.R., et al., "CSF-1-A Mononuclear Phagocyte Lineage-Specific Hemopoietic Growth Factor", (1983), Journal of Cellular Biochemistry 21, pp. 151-159.
Stanley, E.R., et al., "Biology and Action of Colony-Stimulating Factor-1", (1997), Mol. Reprod. Dev. 46, pp. 4-10.
Stanley, E.R., et al., "The Biology and Action of Colony Stimulating Factor-1", (1994), Stem Cells 12(suppl 1), pp. 15-25.
Steidl, C., et al., "Tumor-Associated Macrophages and Survival in Classic Hodgkin's Lymphoma", (2010), N. Engl. J. Med., vol. 362, No. 10, pp. 875-885.
Kooten, C.V., et al., "CD40-CD40 ligand", (2000), Journal of Leukocyte Biology 67, pp. 2-17.
Wang, Z., et al., "Identification of the Ligand-Binding Regions in the Macrophage Colony-Stimulating Factor Receptor Extracellular Domain", (1993), Molecular and Cellular Biology, vol. 13, No. 9, pp. 5348-5359.
West, R.B., et al., "A landscape effect in tenosynovial giant-cell tumor from activation of CSF1 expression by a translocation in a minority of tumor cells", Proc. Natl. Acad. Sci USA, vol. 103, No. 3, pp. 690-695, (2006).
Wu, T.T., et al., "An Analysis of the Sequences of the Variable Regions of Bence Jones Proteins and Myeloma Light Chains and Their Implications for Anti-body Complementarity", (1970), J. Exp. Med. 132, pp. 211-250.
Wyckoff, J.B., et al., "Direct Visualization of Macrophage-Assisted Tumor Cell Intravasation in Mammary Tumors", (2007), Cancer Res., vol. 67, No. 6, pp. 2649-2656.
Yeung, Y.G., et al., "Proteomic Approaches to the Analysis of Early Events in Colony-stimulating Factor-1 Signal Transduction", (2003), Molecular & Cellular Proteomics 2.11, pp. 1143-1155.
Kabat, E.A., "Sequences of Proteins of Immunological Interest", (1991), 5$^{th}$ Edition, Public Health Service, National Institutes of Health, Bethesda, MD, Columbia University (N.Y.), New York, NY USA—(Abstract attached).
Lieberman, H.A., "Pharmaceutical Dosage Forms: Tablets", (1990), 2$^{nd}$ Edition, revised and expanded, vols. 1-3.
Avis, K.E., et al., "Pharmaceutical Dosage Form: Parenteral Medications", (1984), 2$^{nd}$ Edition, revised and expanded, vols. 1 and 2.
Lieberman, H.A., et al., "Pharmaceutical Dosage Form: Disperse Systems", (1996), 2$^{nd}$ Edition, vols. 1 and 2 (Abstract attached).
Bryne et al., "CSF-1R-Dependent Lethal Hepatotoxicity When Agonistic CD40 Antibody is Given before but Not after Chemotherapy.", The Journal of Immunology, Jul. 1, 2016, pp. 179-187, vol. 197(1), XP055340485.
Wiehagen et al., "Combination of 1-40 CD40 Agonism and CSF-1R Blockade Reconditions Tumor-Associated Macrophages and Drives Potent Antitumor Immunity.", Cancer Immunology Research, Nov. 2, 2017, pp. 1109-1121, vol. 5(12), XP055473756.
International Search Report relating to corresponding PCT Patent Application No. PCT/US2018/020575. Mailing Date of International Search Report: dated Jun. 7, 2018.
Written Opinion relating to corresponding PCT Patent Application No. PCT/US2018/020575. Mailing Date of Written Opinion: dated Jun. 7, 2018.

* cited by examiner

CO-THERAPY COMPRISING A SMALL MOLECULE CSF-1R INHIBITOR AND AN AGONISTIC ANTIBODY THAT SPECIFICALLY BINDS CD40 FOR THE TREATMENT OF CANCER

CROSS-REFERENCE TO RELATED APPLICATIONS

This application claims priority to U.S. Provisional Patent Application No. 62/466,503, filed Mar. 3, 2017 and U.S. Provisional Patent Application No. 62/500,313, filed May 2, 2017. The disclosure of each of these patent applications is hereby incorporated by reference in its entirety.

SEQUENCE LISTING

This application contains a Sequence Listing submitted via EFS-Web, the entire content of which is incorporated herein by reference. The ASCII text file, created on 12 Jun. 2018, is named JBI5123USNPharborsequencelisting.txt and is 41.6 kilobytes in size.

FIELD OF THE INVENTION

The present invention is directed to methods for treating cancer, preferably a solid tumor or hematological malignancy, including for example pancreatic cancer, lung cancer (including but not limited to non-small cell lung cancer (NSCLC)), prostate cancer, colorectal cancer, breast cancer, melanoma) or non-Hodgkin's lymphoma, comprising administering to a subject in need thereof a therapeutically effective amount of co-therapy comprising, consisting or consisting essentially of (a) a small molecule CSF-1R inhibitor and (b) an agonistic antibody that binds CD40.

BACKGROUND OF THE INVENTION

Many tumors are characterized by a prominent immune cell infiltrate, including macrophages. Initially, the immune cells were thought to be part of a defense mechanism against the tumor, but recent data support the notion that several immune cell populations including macrophages may, in fact, promote tumor progression. Macrophages are characterized by their plasticity. Depending on the cytokine microenvironment, macrophages can exhibit so-called M1 or M2-subtypes. M2 macrophages are engaged in the suppression of tumor immunity. They also play an important role in tissue repair functions such as angiogenesis and tissue remodeling which are coopted by the tumor to support growth. In contrast to tumor promoting M2 macrophages, M1 macrophages exhibit antitumor activity via the secretion of inflammatory cytokines and their engagement in antigen presentation and phagocytosis (MANTOVANI, A. et al., Curr. Opin. Immunol. 2 (2010) 231-237).

By secreting various cytokines such as colony stimulating factor 1 (CSF-1) and IL-10, tumor cells are able to recruit and shape macrophages into the M2-subtype, whereas cytokines such as granulocyte macrophage colony stimulating factor (GM-CSF), IFN-gamma program macrophages towards the M1 subtype. Using immunohistochemistry, it is possible to distinguish between a macrophage subpopulation co-expressing CD68 and CD163, which is likely to be enriched for M2 Macrophages, and a subset showing the CD68+/MHC II+, or CD68+/CD80+ immunophenotype, likely to include M1 macrophages. Cell shape, size, and spatial distribution of CD68 and CD163 positive macrophages is consistent with published hypotheses on a tumor-promoting role of M2 macrophages, for example by their preferential location in tumor intersecting stroma, and vital tumor areas. In contrast, CD68+/MHC class II+ macrophages are ubiquitously found. Their hypothetical role in phagocytosis is reflected by clusters of the CD68+/MHC class II+, but CD163-immunophenotype near apoptotic cells and necrotic tumor areas.

The subtype and marker expression of different macrophage subpopulations is linked with their functional state. M2 macrophages can support tumorigenesis by: (a) enhancing angiogenesis via the secretion of angiogenic factors such as VEGF or bFGF, (b) supporting metastasis formation via secretion of matrix metalloproteinases (MMPs), growth factors and migratory factors guiding the tumor cells to the blood stream and setting up the metastatic niche (WYCKOFF, J. et al., Cancer Res. 67 (2007) 2649-2656), (c) playing a role in building an immunosuppressive milieu by secreting immunosuppressive cytokines such as IL-4, 11-13, IL-1ra and IL-10, which in turn regulate T regulatory cell function. Conversely CD4 positive T cells have been shown to enhance the activity of tumor promoting macrophages in preclinical models (MANTOVANI, A. et al., Eur. J. Cancer 40 (2004) 1660-1667; DENARDO, D. et al., Cancer Cell 16 (2009) 91-102).

Accordingly, in several types of cancer (e.g. breast, ovarian, Hodgkin's lymphoma) the prevalence of M2 subtype tumor associated macrophages (TAMs) has been associated with poor prognosis (BINGLE, L. et al., J. Pathol. 3 (2002) 254-265; ORRE, M., and ROGERS, P. A., Gynecol. Oncol. 1 (1999) 47-50; STEIDL, C. et al., N. Engl. J. Med. 10 (2010) 875-885). Recent data show a correlation of CD163 positive macrophage infiltrate in tumors and tumor grade (KAWAMURA, K. et al., Pathol. Int. 59 (2009) 300-305). TAMs isolated from patient tumors had a tolerant phenotype and were not cytotoxic to tumor cells (MANTOVAN, A. et al., Eur. J. Cancer 40 (2004) 1660-1667). However, infiltration of TAMs in the presence of cytotoxic T cells correlates with improved survival in non-small cell lung cancer and hence reflects a more prominent M1 macrophage infiltrate in this tumor type (KAWAI, O. et al., Cancer 6 (2008) 1387-1395).

Recently, a so-called immune signature comprising high numbers of macrophages and CD4 positive T cells, but low numbers of cytotoxic CD8 positive T cells was shown to correlate with reduced overall survival (OS) in breast cancer patients and to represent an independent prognostic factor (DENARDO, D. et al., Cancer Discovery 1 (2011) 54-67).

Consistent with a role for CSF-1 in driving the pro-tumorigenic function of M2 macrophages, high CSF-1 expression in rare sarcomas or locally aggressive connective tissue tumors, such as pigmented villonodular synovitis (PVNS) and tenosynovial giant cell tumor (TGCT) due in part to a translocation of the CSF-1 gene, leads to the accumulation of monocytes and macrophages expressing the receptor for CSF-1, the colony-stimulating factor 1 receptor (CSF-1R) forming the majority of the tumor mass (WEST, R. B. et al., Proc. Natl. Acad. Sci. USA 3 (2006) 690-695). These tumors were subsequently used to define a CSF-1 dependent macrophage signature by gene expression profiling. In breast cancer and leiomyosarcoma patient tumors this CSF-1 response gene signature predicts poor prognosis (ESPINOSA, I. et al., Am. J. Pathol. 6 (2009) 2347-2356; Beck, A. et al., Clin. Cancer Res. 3 (2009) 778-787).

The cell surface CD40 molecule is a member of the tumor necrosis factor receptor superfamily (TNFR) and a key regulator in both innate and adaptive immune responses.

CD40 is expressed on human antigen presenting cells, in particular B cells, dendritic cells and macrophages, as well as on fibroblasts, smooth muscle cells, endothelial cells and epithelial cells. CD40 is also expressed on a wide range of tumor cells including all B-lymphomas, 30-70% of solid tumors, melanomas and carcinomas.

The natural ligand of CD40, designated CD154 or CD40L, is mainly expressed on activated T lymphocytes and platelets. The interaction of CD40 with CD40L on T cells induces both humoral and cell-mediated immune responses. CD40 regulates this ligand-receptor pair to activate B cells and other antigen-presenting cells (APC) including dendritic cells (DCs), driving T cell activation. For example, activation of CD40 on B cells induces B cell proliferation, somatic hypermutation, differentiation into antibody secreting cells and isotype switching in germinal centers of secondary lymphoid organs. In vitro studies have shown direct effects of CD40 activation on cytokine production (e.g. IL-6, IL-10, IL-12, TNF-α), expression of adhesion molecules and costimulatory receptors (e.g. ICAM, CD23, CD80 and CD86), and increased expression of MHC class I, MHC class II, and TAP transporter by B lymphocytes.

CD40 antibodies may elicit their antitumor effects by various mechanisms, including activation of antigen presenting cells resulting in increased activity of tumor specific cytotoxic T lymphocytes and natural killer cells (NK cells), or direct antibody-mediated tumor cell apoptosis or cellular cytotoxicity of CD40 positive tumors. Systemic administration of anti-CD40 antibodies has however also been associated with adverse side effects, such as a cytokine release syndrome.

The human CSF-1 receptor (CSF-1R; colony stimulating factor 1 receptor; synonyms: M-CSF receptor; Macrophage colony-stimulating factor 1 receptor, Fms proto-oncogene, cFMS) is known since 1986 (COUSSENS, L., et al., Nature 320 (1986) 277-280). CSF-1R is a growth factor and encoded by the cFMS proto-oncogene (reviewed e. g. in ROTH, P., and STANLEY, E. R., Curr. Top. Microbiol. Immunol. 181 (1992) 141-167).

CSF-1R is the receptor for CSF-1 (colony stimulating factor 1, also called M-CSF, macrophage colony-stimulating factor) and mediates the biological effects of this cytokine (SHERR, C. J., et al., Cell 41 (1985) 665-676). The cloning of the colony stimulating factor-1 receptor (CSF-1R) (also called cfms) was described for the first time in ROUSSEL, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cb1 and thereby regulates receptor down regulation (LEE, P. S., et al., Embo J. 18 (1999) 3616-3628). A second ligand for CSF-1R termed interleukin-34 (IL-34) was identified (LIN, H., et al, Science 320 (2008) 807-811).

Two CSF-1R ligands that bind to the extracellular domain of CSF-1R are known. The first one is CSF-1 (colony stimulating factor 1, also called M-CSF, macrophage) which is found extracellularly as a disulfide linked homodimer (STANLEY, E. R. et al., Journal of Cellular Biochemistry 21 (1983) 151-159; STANLEY, E. R. et al., Stem Cells 12 Suppl. 1 (1995) 15-24). The second is IL-34 (Human IL-34) (HUME, D. A., et al, Blood 119 (2012) 1810-1820). The main biological effects of CSF-1R signaling are the differentiation, proliferation, migration, and survival of hematopoietic precursor cells to the macrophage lineage (including osteoclast). Activation of CSF-1R is mediated by its CSF-1R ligands, CSF-1 (M-CSF) and IL-34. Binding of CSF-1 (M-CSF) to CSF-1R induces the formation of homodimers and activation of the kinase by tyrosine phosphorylation (LI, W. et al, EMBO Journal. 10 (1991) 277-288; STANLEY, E. R., et al., Mol. Reprod. Dev. 46 (1997) 4-10).

The biologically active homodimer CSF-1 binds to the CSF-1R within the subdomains D1 to D3 of the extracellular domain of the CSF-1 receptor (CSF-1R-ECD). The CSF-1R-ECD comprises five immunoglobulin-like subdomains (designated D1 to D5). The subdomains D4 to D5 of the extracellular domain (CSF-1R-ECD) are not involved in the CSF-1 binding (WANG, Z., et al Molecular and Cellular Biology 13 (1993) 5348-5359). The subdomain D4 is involved in dimerization (YEUNG, Y-G., et al Molecular & Cellular Proteomics 2 (2003) 1143-1155; PIXLEY, F. J., et al., Trends Cell Biol 14 (2004) 628-638).

Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STATI, STAT3, PLCy, and Cb1 (BOURETTE, R. P. and ROHRSCHNEIDER, L. R., Growth Factors 17 (2000) 155-166).

CSF-1R signaling has a physiological role in immune responses, in bone remodeling and in the reproductive system. The knockout animals for either CSF-1 (POLLARD, J. W., Mol. Reprod. Dev. 46 (1997) 54-61) or CSF-1R (DAI, X. M., et al., Blood 99 (2002) 111-120) have been shown to have osteopetrotic, hematopoietic, tissue macrophage, and reproductive phenotypes consistent With a role for CSF-1R in the respective cell types.

CSF-1R is a protein encoded by the CSF-1R gene. It controls the production, differentiation, and function of M2 macrophages, which, in turn, support tumor growth and metastasis formation and secrete immunosuppressive cytokines, leading to a poor prognosis in patients. Furthermore, presence of CSF-1R positive macrophages in several human cancers (such as ovarian and breast carcinoma) has been shown to correlate not only with increased vascular density but also worse clinical outcome. CSF-1R inhibitors, which selectively inhibit M2-like TAMs, have demonstrated activity in preclinical models (DENARDO, D. et al., Cancer Discovery 1 (2011) 54-67; LIN, E. et al., J. Exp. Med. 193 (2001) 727-740). Blockade of CSF-1R activity results in reduced recruitment of TAMs and, in combination with chemotherapy, a synergistic action results in reduced tumor growth and metastatic burden. Recent data have shown that in patients with PVNS and TGCT, overexpression of the CSF-1 is detected and is in part mediated by a translocation of the CSF-1R gene (WEST, R. B. et al., Proc. Natl. Acad. Sci. USA 3 (2006) 690-695). In breast cancer the presence of a CSF-1 response gene signature predicts risk of recurrence and metastasis (BECK, A. et al., Clin. Cancer Res. 3 (2009) 778-787).

CANNARILE, M., et al., in US Patent Publication US2014/0079706 A1, published Mar. 20, 2014 describe the combination therapy of antibodies binding to humans CSF-1R, in combination with a chemotherapeutic agent, radiation and/or cancer immunotherapy.

There remains a need for pharmaceutical therapies for treating various cancers, including solid tumors and liquid tumors, such as pancreatic cancer, prostate cancers, colorectal cancer, lung cancers (including and non-small cell lung cancer), breast cancer, non-Hodgkin's lymphoma and melanoma.

SUMMARY OF THE INVENTION

The present invention provides methods for treating cancer, preferably a solid tumor or hematological malignancy, wherein the solid tumor includes, for example, pancreatic cancer, lung cancer (including but not limited to non-small cell lung cancer (NSCLC)), prostate cancer, colorectal cancer, breast cancer and melanoma; and wherein the hematological malignancy includes, for example, non-Hodgkin's lymphoma, comprising administering to a subject in need thereof a therapeutically effective amount of co-therapy comprising, consisting or consisting essentially of (a) a small molecule CSF-1R inhibitor and (b) an agonistic antibody that specifically binds CD40.

The present invention also provides methods for treating cancer, including for example pancreatic cancer, lung cancer (including but not limited to non-small cell lung cancer (NSCLC)), prostate cancer, colorectal cancer, breast cancer, melanoma or non-Hodgkin's lymphoma, comprising administering to a subject in need thereof a therapeutically effective amount of co-therapy comprising, (a) a small molecule CSF-1R inhibitor and (b) an agonistic antibody that specifically binds CD40, wherein the co-therapy is administered to the patient in conjunction with (preferably concurrently or consecutively) at least one additional therapy, such as radiation, a radiopharmaceutical regimen, a second chemotherapy regimen and/or an immunotherapy regimen.

DETAILED DESCRIPTION OF THE INVENTION

The present invention is directed to methods for treating cancer (preferably a solid tumor or a hematological malignancy), including for example pancreatic cancer, lung cancer (including but not limited to non-small cell lung cancer (NSCLC)), prostate cancer, colorectal cancer, breast cancer, melanoma or non-Hodgkin's lymphoma, comprising administering to a subject in need thereof a therapeutically effective amount of co-therapy comprising, consisting or consisting essentially of (a) a small molecule CSF-1R inhibitor and (b) an agonistic antibody that specifically binds CD40.

In an embodiment, the present invention is directed to methods for treating cancer, wherein the cancer is selected from the group consisting of pancreatic cancer, non-small cell lung cancer (NSCLC), prostate cancer and colorectal cancer.

In an embodiment, the present invention is directed to methods for treating pancreatic cancer. In another embodiment, the present invention is directed to methods for treating non-small cell lung cancer. In another embodiment, the present invention is directed to methods for treating prostate cancer. In another embodiment, the present invention is directed to methods for treating colorectal cancer.

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein.

As used herein, the singular forms "a," "and," and "the" include plural reference unless the context clearly dictates otherwise.

Further, to provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Abbreviations used in the specification, particularly the Examples which follow herein, are as follows:

bid×14=twice daily (dosing) with one dose on Day 1 biwk=twice weekly (biweekly)

BW=body weight i.p.=intraperitoneal(ly)

HPMC=hydroxypropyl methylcellulose

MTV=median tumor volume

NTR=non-treatment-related (death)

NTRu=non-treatment-related (death) due to unknown etiology p.o.=oral(ly)

TFS=tumor-free survivor

TGD=tumor growth delay

TGI=tumor growth inhibition

TP=euthanized for tumor progression

TR=treatment-related (death)

TTE=time-to-endpoint

Vehicle=0.5% Methocel F4M (HPMC)

As used herein, unless otherwise noted, the terms "small molecule CSF-1R inhibitor" and "CSF-1R small molecule" shall mean a chemically synthesized pharmaceutical agent (e.g. a biologically active agent) of defined chemical structure. Preferably, the small molecule CSF-1R inhibitor is an organic compound of defined structure with a molecular weight of less than or equal to 900 daltons, more preferably less than or equal to 500 daltons.

Suitable examples of small molecule CSF-1R inhibitors include, but are not limited to AB-530, also known as N-[4-[3-(5-tert-Butyl-1,2-oxazol-3-yl)ureido]phenyl]imidazo[2,1-b]benzothiazole-2-carboxamide (Daiichi Sankyo), AC-708 (Ambit Bioscience), AC-710 (Ambit Bioscience), AC-855 (Ambit Bioscience), ARRY-382 (Array BioPharma), AZ-683 (Astra-Zeneca), AZD-6495 (Astra Zenenca), BLZ-3495 (Novartis), BLZ-945 (Novartis), N-(4-[[(5-tert-Butyl-1,2-oxazol-3-yl)carbamoyl]amino]phenyl)-5-[(1,2,2,6,6-pentamethylpiperidin-4-yl)oxy]pyridine-2-carboxamide methanesulfonate (Daiichi Sankyo), N-(4-[[(5-tert-Butyl-1,2-oxazol-3-yl)carbamoyl]amino]phenyl)-5-[(1,2,2,6,6-pentamethylpiperidin-4-yl)oxy]pyridine-2-carboxamide methanesulfonate (Diaiichi Sankyo), CT 1578 (CTI BioPharma), CYT-645 (Gilead), DCC 2909 (Deciphera), DCC-3014 (Deciphera), DP-4577 (Deciphera), DP-5599 (Deciphera), DP-6261 (Deciphera), ENMD-981693 (EntreMed), FMS kinase inhibitors (AEgera), GT-79 (Gerinda Therapeutics), GW-2580 also known as 5-[3-Methoxy-4-(4-methoxybenzyloxy)benzyl]pyrimidine-2,4-diamine (GlaxoSmithKline), Ilorasertib (University of Chicago), Ki-20227 (Kyowa Hakko Kirin), Linifanib (AbbVie), Masitinib (AB Science), Pexidartinib (Plexxikon), PLX 5622 (Plexxikon), PLX FK1 (Plexxikon), PLX-7486 (Plexxikon), REDX-05182 (Redx Oncology), 5-cyano-N-[2-(cyclohexen-1-yl)-4-[1-[2-(dimethylamino)acetyl]piperidin-4-yl]phenyl]-1H-imidazole-2-carboxamide, and the compound of formula (I)

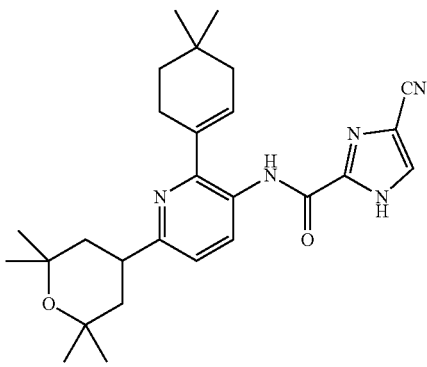

also known as 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide or a solvate, hydrate, tautomer, or pharmaceutically acceptable salt thereof (Johnson & Johnson, Illig, C., et al., in US Patent Publication US2009/0105296 A1, published Apr. 23, 2009).

In certain embodiments, the small molecule CSF-1R inhibitor is selected from the group consisting of AB-530, also known as N-[4-[3-(5-tert-Butyl-1,2-oxazol-3-yl)ureido]phenyl]imidazo[2,1-b]benzothiazole-2-carboxamide (Daiichi Sankyo), AC-708 (Ambit Bioscience), AC-710 (Ambit Bioscience), AC-855 (Ambit Bioscience), BLZ-3495 (Novartis), DCC-3014 (Deciphera), GW-2580 also known as 5-[3-Methoxy-4-(4-methoxybenzyloxy)benzyl]pyrimidine-2,4-diamine (GlaxoSmithKline), Ilorasertib (University of ChicagoMasitinib (AB Science), Pexidartinib (Plexxikon), PLX 5622 (Plexxikon), PLX FK1 (Plexxikon), PLX-7486 (Plexxikon), REDX-05182 (Redx Oncology), and the compound of formula (I)

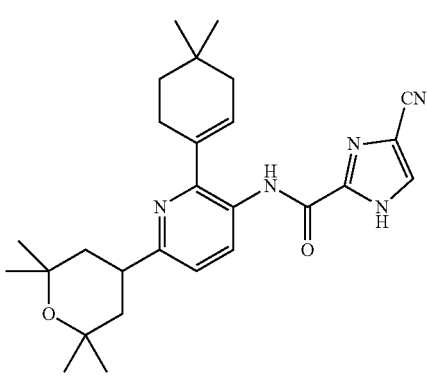

also known as 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide or a solvate, hydrate, tautomer, or pharmaceutically acceptable salt thereof.

In certain embodiments of the present invention, the small molecule CSF-1R inhibitor is selected from the group consisting of a compound of formula (I) or a solvate, hydrate, tautomer or pharmaceutically acceptable salt thereof, PLX-3397 (PLexxikon), DCC-3014 (Deciphera) and BLZ-3495 (Novartis).

In certain embodiments of the present invention, the small molecule CFS-1R inhibitor is selected from the group consisting of PLX-3397 (PLexxikon), DCC-3014 (Deciphera) and BLZ-3495 (Novartis).

In certain embodiments of the present invention, the small molecule CFS-1R inhibitor is the compound of formula (I) or a solvate, hydrate, tautomer or pharmaceutically acceptable salt thereof.

The compound of formula (I) is a protein tyrosine kinase inhibitor, more particularly an inhibitor of cFMS kinase. As disclosed in ILLIG, C., et al., US Patent Publication US2009/0105296 A1, the cFMS kinase inhibitor of formula (I) is useful for the treatment of diseases including, but not limited to: osteoporosis, Paget's disease, rheumatoid arthritis, other forms of inflammatory arthritis, osteoarthritis, prosthesis failure, osteolytic sarcoma, myeloma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis.

In certain embodiments of the present invention, the compound of formula (I) is administered in an amount in the range of from about 10 mg per day to about 1000 mg per day, in one or more doses. In another embodiment of the present invention, the compound of formula (I) is administered in an amount in the range of from about 50 mg per day to about 600 mg per day, in one or more doses. In another embodiment of the present invention, the compound of formula (I) is administered in an amount in the range of from about 50 mg per day to about 300 mg per day, in one or more doses. In another embodiment of the present invention, the compound of formula (I) is administered in an amount in the range of from about 100 mg per day to about 200 mg per day, in one or more doses. In another embodiment of the present invention, the compound of formula (I) is administered in an amount of about 50 mg per day, about 100 mg per day, about 150 mg per day, about 200 mg per day, about 250 mg per day, about 300 mg per day or about 600 mg per day, preferably in an amount of about 100 mg per day, about 150 mg per day or about 200 mg per day.

One skilled in the art will readily recognize that recommended dosage amounts and regiments for known and/or marketed small molecule CSF-1R inhibitors are known or may be determined by consulting appropriate references such as drug package inserts, FDA guidelines, the Physician's Desk Reference, and the like.

"Specific binding" or "specifically binds" or "binds" when referring to an antibody shall mean an antibody that specifically binds CD40 with greater affinity than for non-related antigens. Typically, the antibody binds CD40 with a dissociation constant ($K_D$) of about $1 \times 10^{-8}$ M or less, for example about $1 \times 10^{-9}$ M or less, about $1 \times 10^{-10}$ M or less, about $1 \times 10^{-11}$ M or less, or about $1 \times 10^{-12}$ M or less, typically with the $K_D$ that is at least one hundred fold less than its $K_D$ for binding to a non-related antigen (for example, BSA, casein). The dissociation constant may be measured using standard procedures. Antibodies that bind CD40 may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset).

As used herein, unless otherwise noted, the term "antibodies" is meant in a broad sense and includes immunoglobulin molecules including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy (H) chains and two light (L) chains inter-connected by disulfide bonds as well as multimers thereof (for example IgM). Each heavy chain is comprised of a heavy chain variable region (VH) and a heavy chain constant region (comprised of domains CH1, hinge CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4.

As used herein, unless otherwise noted, the term "complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Wu (WU et al. (1970) *J Exp Med* 132: 211-50), Kabat (KABAT et al., Sequences of Proteins of Immunological Interest, 5th Ed. Public Health Service, National Institutes of Health, Bethesda, Md., 1991), Chothia (CHOTHIA et al. (1987) *J Mol Biol* 196: 901-17) and IMGT (LEFRANC et al. (2003) *Dev Comp Immunol* 27: 55-77). The correspondence between the various delineations and variable region numbering are described (see e.g. LEFRANC et al. (2003) *Dev Comp Immunol* 27: 55-77; HONEGGER and PLUCKTHUN, *J Mol Biol* (2001) 309: 657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species can be assigned to one of two clearly distinct types, namely kappa (κ) and lambda (λ), based on the amino acid sequences of their constant domains.

As used herein, unless otherwise noted, the term "antigen-binding fragment" refers to a portion of an immunoglobulin molecule that retains the antigen binding properties of the parental full length antibody. Exemplary antigen-binding fragments are heavy chain complementarity determining regions (HCDR) 1, 2 and/or 3, light chain complementarity determining regions (LCDR) 1, 2 and/or 3, a heavy chain variable region (VH), or a light chain variable region (VL), Fab, F(ab')2, Fd and Fv fragments as well as domain antibodies (dAb) consisting of either one VH domain or one VL domain. VH and VL domains may be linked together via a synthetic linker to form various types of single chain antibody designs in which the VH/VL domains pair intramolecularly or intermolecularly in those cases when the VH and VL domains are expressed by separate chains to form a monovalent antigen binding fragments, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

As used herein, unless otherwise noted, the term "monoclonal antibody" refers to an antibody population with single amino acid composition in each heavy and each light chain, except for possible well known alterations such as removal of C-terminal lysine from the antibody heavy chain. Monoclonal antibodies typically bind one antigenic epitope, except that multispecific monoclonal antibodies bind two or more distinct antigens or epitopes. Bispecific monoclonal antibodies bind two distinct antigenic epitopes. Monoclonal antibodies may have heterogeneous glycosylation within the antibody population. Monoclonal antibodies may be monospecific or multispecific, or monovalent, bivalent or multivalent. A multispecific antibody, such as a bispecific antibody or a trispecific antibody is included in the term monoclonal antibody.

As used herein, unless otherwise noted, the term "isolated antibody" refers to an antibody or an antigen-binding fragment thereof that has been separated and/or recovered from other components of the system the antibody is produced in, such as a recombinant cell, as well as an antibody that has been subjected to at least one purification or isolation step. The isolated antibody may be substantially free of other cellular material and/or chemicals. "Isolated antibody" encompasses antibodies that are isolated to a higher purity, such as antibodies that are 80%, 81%, 82%, 83%, 84%, 85%, 86%, 87%, 88%, 89%, 90%, 91%, 92%, 93%, 94%, 95%, 96%, 97%, 98%, 99% or 100% pure.

As used herein, unless otherwise noted, the term "humanized antibodies" refers to antibodies in which CDR sequences are derived from non-human species and the frameworks are derived from human immunoglobulin sequences. Humanized antibodies may include intentionally introduced mutations in the framework regions so that the framework may not be an exact copy of expressed human immunoglobulin or germline gene sequences.

As used herein, unless otherwise noted, the term "human antibodies" refers to antibodies that are optimized to have minimal immune response when administered to a human subject. Variable regions of human antibodies are derived from human germline immunoglobulin sequences. If the antibodies contain a constant region or a portion of the constant region, the constant region is also derived from human germline immunoglobulin sequences.

A human antibody comprises heavy or light chain variable regions that are derived from sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci as described herein. A human antibody typically contains amino acid differences when compared to the immunoglobulins expressed in humans due to, for example introduction of somatic mutations intentional introduction of substitutions into the framework or antigen binding site and amino acid changes introduced during cloning and VDJ recombination in non-human animals. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, a human antibody may contain consensus framework sequences derived from human framework sequence analyses, for example as described in KNAPPIK et al., J Mol Biol 296:57-86, 2000, or synthetic HCDR3 incorporated into human immunoglobulin gene libraries displayed on phage, for example as described in SHI et al., J Mol Biol, 397:385-96, 2010 and Int. Pat. Publ. No. WO2009/085462.

As used herein, unless otherwise noted, the term "epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

As used herein, unless otherwise noted, the term "CD40" or "huCD40" refers to the human CD40 protein. CD40 is also known as Tumor necrosis factor receptor superfamily member 5 (TNFRSF5), CD40L receptor or CD154 receptor. The amino acid sequence of the full length human CD40 is shown in SEQ ID NO: 1. Human full length CD40 protein is a type I membrane protein with 277 amino acids. Signal sequence spans residues 1-20, extracellular domain spans residues 21-193, transmembrane domain spans residues 194-215, and cytoplasmic domain spans residues 216-277 of SEQ ID NO: 1.

As used herein, unless otherwise noted, the term "agonist" or "agonistic" when describing an antibody refers to an antibody that induces B-cell and/or dendritic cell (DC) activation upon binding to CD40. B cell and DC activation may be measured by measuring increased B cell proliferation, by measuring up-regulation of one or more of the surface markers CD23, CD80, CD83, CD86 and HLA-DR on B cells or CD80, CD83, CD86 and HLA-DR on DC, or by measuring production of one or more cytokines such as IL-6, IL-10, IL-12 or TNF-α. The agonist may induce B-cell and/or DC activation in a statistically significant manner when compared to a control sample without the antibody.

As used herein, unless otherwise noted, the term "cross-linking" refers to the higher order multimerization of CD40 on cells induced by binding of an antibody that specifically binds CD40 to FcγRIIb cis or trans, resulting in induction of CD40 agonistic activity.

As used herein, unless otherwise noted, the term "requires cross linking for agonistic activity" means that the antibody induces CD23 expression on B cells and/or CD83 surface expression on dendritic cells in the presence of cross-linker anti-human F(ab')2 at 20 µg/ml in a dose-dependent manner, and that the antibody has no effect on CD23 surface expression on B cells and CD83 surface expression on dendritic cells in the absence of the cross-linker, when surface expression is measured using flow cytometry. No effect means that the signal obtained in flow cytometry indicative of surface expression of CD23 and CD83 is within ±1 SD across antibody titration curve at antibody concentrations ranging from $1\times10^{-12}$ M to $1\times10^{-6}$ M.

The present invention is directed to methods for treating cancer (preferably a solid tumor or a hematological malignancy), comprising administering a therapeutically effective amount of co-therapy comprising (a) a small molecule CSF-1R inhibitor and (b) an agonistic antibody that specifically binds CD-40; optionally in combination with radiation and/at least one additional therapeutic agent, preferably anti-cancer therapeutic agent(s).

The term "subject" as used herein, refers to an animal, preferably a mammal, most preferably a human, who has been the object of treatment, observation. Preferably, the subject has experienced and/or exhibited at least one symptom of the disease or disorder to be treated and/or prevented. In certain embodiments, the "subject" is a subject in need of treatment, including subjects who already exhibit the undesired physiological change or diseases, well as those subjects prone to have the physiological change or disease.

As used herein, unless otherwise noted, the terms "treating", "treatment" and the like, shall include the management and care of a subject or patient (preferably a mammal, more preferably a human) for the purpose of combating a disease, condition, or disorder. The terms "treating" and "treatment" include the administration of combination therapy or co-therapy, compound(s) or pharmaceutical composition(s) as described herein to (a) alleviate one or more symptoms or complications of the disease, condition or disorder; (b) prevent the onset of one or more symptoms or complications of the disease, condition or disorder; and/or (c) eliminate one or more symptoms or complications of the disease, condition, or disorder.

Additionally, the terms "treat" or "treatment" refer to treatment wherein the object is to slow down (lessen) an undesired physiological change or disease, such as the development or spread of tumor or tumor cells, or to provide a beneficial or desired clinical outcome during treatment. Beneficial or desired clinical outcomes include alleviation of symptoms, diminishment of extent of disease, stabilized (i.e., not worsening) state of disease, delay or slowing of disease progression, lack of metastasis, amelioration or palliation of the disease state, and remission (whether partial or total), whether detectable or undetectable. "Treatment" may also mean prolonging survival as compared to expected survival if a subject was not receiving treatment.

In certain embodiments of the present invention, the methods of treating cancer include inhibiting the proliferation of tumor cells (preferably solid tumor cells or hematological malignancy cells). In certain embodiments of the present invention, the methods of treating cancer include inhibiting metastasis of a tumor (preferably a solid tumor or hematological malignancy such as non-Hodgkin's lymphoma).

As used herein, the terms "co-therapy" and "combination therapy" shall mean treatment of a subject in need thereof by administering (a) a small molecule CSF-1R inhibitor and (b) an agonistic antibody that specifically binds CD40, wherein (a) the small molecule CSF-1R inhibitor and (b) the agonistic antibody that specifically binds CD40 are administered by any suitable means, simultaneously, sequentially, separately or in a single pharmaceutical formulation. Where the (a) small molecule CSF-1R inhibitor and the (b) agonistic antibody that specifically binds CD40 are administered in separate dosage forms, the number of dosages administered for each compound may be the same or different. The (a) small molecule CSF-1R inhibitor and the (b) agonistic antibody that specifically binds CD40 may be administered via the same or different route of administration. Examples of suitable methods of administration include, but are not limited to, oral, intravenous (iv), intramuscular (im), subcutaneous (sc), transdermal, intratumoral, and rectal. The (a) small molecule CSF-1R inhibitor and the (b) agonistic antibody that specifically binds CD40 may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The (a) small molecule CSF-1R inhibitor and the (b) agonistic antibody that specifically binds CD40 may be administered according to simultaneous or alternating regimens, at the same or different times during the course of the therapy, concurrently in divided or single forms.

As used herein, unless otherwise noted, the term "therapeutically effective amount" means that amount of active compound(s), pharmaceutical agent(s), co-therapy or combination therapy that elicits the biological or medicinal response in a tissue system, animal or human that is being sought by a researcher, veterinarian, medical doctor or other clinician, which includes alleviation of the symptoms of the disease or disorder being treated.

In certain embodiment of the present invention, exemplary indicators of the therapeutically effective amount include, for example, improved well-being of the patient, reduction in tumor burden, arrested or slowed growth of a tumor, and/or absence of metastasis of cancer cells to other locations in the body.

Wherein the present invention is directed to co-therapy or combination therapy, "therapeutically effective amount" shall mean the amount of the combination of agents taken together, such that the combined effect elicits the desired biological or medicinal response. For example, the therapeutically effective amount of co-therapy comprising administration of (a) a small molecule CSF-1R inhibitor and (b) an agonistic antibody that specifically binds CD40, would be the amount of (a) a small molecule CSF-1R inhibitor and (b) an agonistic antibody that specifically binds CD40 that when taken together or separately have a combined effect that is therapeutically effective. Further, it will be recognized by one skilled in the art that in the case of co-therapy or combination therapy with a therapeutically effective amount, as in the example above, the amount of the (a) small molecule CSF-1R inhibitor and/or the amount of the (b) agonistic antibody that specifically binds CD40 individually may or may not be therapeutically effective.

Optimal dosages (for a small molecule CSF-1R inhibitor, an agonistic antibody that specifically binds CD40, or co-therapy comprising a small molecule CSF-1R inhibitor and an agonistic antibody that specifically binds CD40) to be administered may be readily determined by those skilled in the art, and will vary with for example, the mode of administration, the strength of the preparation, and the advancement of the disease condition. In addition, factors associated with the particular patient being treated, including patient age, weight, diet and time of administration, will result in the need to adjust dosages.

The present invention is directed to combination therapy or co-therapy as described herein. In certain embodiments of the present invention, the combination therapy or co-therapy is advantageous because in certain instances, the administration of the combination of active ingredients achieves a therapeutic effect that is greater than the therapeutic effect achieved by administration of only a single therapeutic agent.

In certain embodiments of the present invention, the co-administration (combination therapy or co-therapy) of two or more therapeutic agents achieves a therapeutic effect that is greater than the therapeutic effect achieved by administration of only a single therapeutic agent. In this regard, the therapeutic effect of one therapeutic agent is augmented by the co-administration of another therapeutic agent. In certain embodiments, the co-administration of two or more therapeutic agents achieves a therapeutic effect that is equal to about the sum of the therapeutic effects achieved by administration of each single therapeutic agent. In these embodiments, the combination therapies are said to be "additive." In certain embodiments, the co-administration of two or more therapeutic agents achieves a synergistic effect, i.e., a therapeutic effect that is greater than the sum of the therapeutic effects of the individual components of the combination.

The therapeutic agents of the co-therapy or combination therapy of the present invention may be administered as separate compositions, e.g., as separate tablets or solutions. One or more active agent may be administered at the same time as the other active agent(s) or the active agents may be administered intermittently. The length of time between administrations of the therapeutic agents may be adjusted to achieve the desired therapeutic effect. In certain instances, one or more therapeutic agent(s) may be administered only a few minutes (e.g., about 1, 2, 5, 10, 30, or 60 min) after administration of the other therapeutic agent(s). Alternatively, one or more therapeutic agent(s) may be administered several hours (e.g., about 2, 4, 6, 10, 12, 24, or 36 hr) after administration of the other therapeutic agent(s). In certain embodiments, it may be advantageous to administer more than one dosage of one or more therapeutic agent(s) between administrations of the remaining therapeutic agent (s). For example, one therapeutic agent may be administered at once daily for between 3 and 21 days (preferably between 5 and 18 days, more preferably between 7 and 14 days) prior to administration of the other therapeutic agent(s). In certain embodiments of the present invention, it is preferred that the therapeutic effects of each active ingredient overlap for at least a portion of the duration of each therapeutic agent so that the overall therapeutic effect of the combination therapy is attributable in part to the combined or synergistic effects of the combination therapy.

Since two or more different active agents are being used together in the combination therapy or co-therapy of the present invention, the potency of each agent and the interactive effects achieved using them together must be considered. The determination of dosage ranges and optimal dosages for a particular mammal is also well within the ability of one of ordinary skill in the art having the benefit of the instant disclosure.

The term "synergistic" refers to a combination which is more effective than the additive effects of any two or more single therapeutic agents. A synergistic effect permits the effective treatment of a disease, disorder or condition using lower amounts (doses) of individual therapeutics. The lower doses may result in lower toxicity (and/or reduced adverse events or severity of adverse events) without reduced efficacy. Alternatively, a synergistic effect can result in improved efficacy. Alternatively still, synergy may result in an improved avoidance or reduction of disease as compared to any single therapy.

Combination therapy or co-therapy can allow for the product of lower doses of the first therapeutic or the second therapeutic agent (referred to as "apparent one-way synergy" herein), or lower doses of both therapeutic agents (referred to as "two-way synergy" herein) than would normally be required when either drug is used alone. In certain embodiments, the synergism exhibited between one or more therapeutic agent(s) and the remaining therapeutic agent(s) is such that the dosage of one of the therapeutic agents would be sub-therapeutic if administered without the dosage of the other therapeutic agent(s).

The terms "augmentation" or "augment" refer to combinations where one of the compounds increases or enhances therapeutic effects of another compound or compounds administered to a patient. In some instances, augmentation can result in improving the efficacy, tolerability, or safety, or any combination thereof, of a particular therapy.

In certain embodiments, the present invention is directed in part to synergistic combinations of one or more therapeutic agent(s) in an amount sufficient to render a therapeutic effect together with the remaining therapeutic agent(s). For example, in certain embodiments a therapeutic effect is attained which is at least about 2 (or at least about 4, 6, 8, or 10) times greater than that obtained with the dose of the one or more therapeutic agent(s) alone. In certain embodiments, the synergistic combination provides a therapeutic effect which is up to about 20, 30 or 40 times greater than that obtained with the dose of the one or more therapeutic agent(s) alone. In such embodiments, the synergistic combinations display what is referred to herein as an "apparent one-way synergy", meaning that the dose of the remaining therapeutic agent(s) synergistically potentiates the effect of the one or more therapeutic agent(s), but the dose of the one or more therapeutic agent(s) does not appear to significantly potentiate the effect of the remaining therapeutic agent(s).

In certain embodiments, the combination of active agents exhibits two-way synergism, meaning that the second therapeutic agent potentiates the effect of the first therapeutic agent, and the first therapeutic agent potentiates the effect of the second therapeutic agent. Thus, other embodiments of the invention relate to combinations of a second therapeutic agent and a first therapeutic agent where the dose of each drug is reduced due to the synergism between the drugs, and the therapeutic effect derived from the combination of drugs in reduced doses is enhanced. The two-way synergism is not always readily apparent in actual dosages due to the potency ratio of the first therapeutic agent to the second therapeutic agent. For instance, two-way synergism can be difficult to detect when one therapeutic agent displays much greater therapeutic potency relative to the other therapeutic agent.

As used herein, the term "composition" is intended to encompass a product comprising the specified ingredients in the specified amounts, as well as any product which results, directly or indirectly, from combinations of the specified ingredients in the specified amounts.

As used herein, in the methods of the present invention, the term "cancer cell", "tumor cell", "cancer" or 'tumor" shall refer to a cancerous, pre-cancerous or transformed cell or tissue, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo (FRESHNEY, Culture of Animal Cells: A Manual of Basic Technique (3rd ed. 1994)).

In certain embodiments of the present invention, the term "cancer" shall include any cancer or tumor whose growth, proliferation and/or metastasis is inhibited or prevented by treatment with an agonistic antibody that specifically binds CD-40 and/or small molecule CSF-1R inhibitor. In an embodiment of the present invention, the cancer is a solid tumor. In an embodiment of the present invention, the cancer is a hematological malignancy.

As used herein, unless otherwise noted, the term "hematological malignancy" shall include cancers that affect the blood and lymph system, which may begin in blood-forming tissue (e.g., bone marrow), or in the cells of the immune system. Hematological malignancies include, but are not limited to leukemia (including, but not limited, acute myeloid leukemia), lymphoma (including, but not limited to, non-Hodgkin's lymphoma and Hodgkin's lymphoma) and multiple myeloma.

In some embodiments, the cancer is a solid tumor.

In some embodiments, the cancer is a hematological malignancy.

In some embodiments, the solid tumor is a prostate cancer, a breast cancer, a colorectal cancer, a pancreatic cancer, an ovarian cancer, a lung cancer, a cervical cancer, a rhabdomyosarcoma, a neuroblastoma, a melanoma, a bladder cancer, or a head and neck cancer.

In some embodiments, the solid tumor is a pancreatic cancer.

In some embodiments, the solid tumor is a lung cancer. In some embodiments, the solid tumor is a squamous non-small cell lung cancer (NSCLC). In some embodiments, the solid tumor is a non-squamous NSCLC. In some embodiments, the solid tumor is a lung adenocarcinoma.

In some embodiments, the solid tumor is a colorectal cancer.

In some embodiments, the solid tumor is a prostate cancer or castration-resistant prostate cancer.

In some embodiments, the solid tumor is a melanoma.

In some embodiments, the solid tumor is a renal cell carcinoma (RCC) (e.g., a kidney clear cell carcinoma or a kidney papillary cell carcinoma), or a metastatic lesion thereof.

In some embodiments, the solid tumor is a mesothelioma. In some embodiments, the solid tumor is a nasopharyngeal carcinoma (NPC).

In some embodiments, the solid tumor is a stomach cancer. In some embodiments, the solid tumor is a gastric cancer. In some embodiments, the solid tumor is a liver cancer.

In some embodiments, the solid tumor is a thyroid cancer. In some embodiments, the solid tumor is a squamous cell carcinoma of the head and neck.

In some embodiments, the solid tumor is a carcinoma of the esophagus or gastrointestinal tract.

In some embodiments, the solid tumor is a breast cancer.

In some embodiments, the solid tumor is an ovarian cancer. In some embodiments, the solid tumor is a fallopian tube cancer. In some embodiments, the solid tumor is an urethral cancer.

In some embodiments, the solid tumor is a brain cancer.

In some embodiments, the hematological malignancy is leukemia.

In some embodiments, the hematological malignancy is lymphoma.

In some embodiments, the hematological malignancy is multiple myeloma.

In some embodiments, the hematological malignancy is non-Hodgkin's lymphoma.

The present invention provides a method of treating a cancer, comprising administering to a subject in need thereof a therapeutically effective amount of co-therapy or combination therapy comprising, consisting to consisting essentially of (a) a small molecule CSF-1R inhibitor and (b) an agonistic antibody or an antigen-binding fragment thereof that specifically binds CD40 for a time sufficient to treat the cancer.

In some embodiments, the agonistic antibody or the antigen-binding fragment thereof that specifically binds CD40 requires cross-linking for agonistic activity.

The agonistic antibodies that specifically bind CD40 requiring cross-linking for their agonistic activity may have decreased cytokine release syndrome (CRS)-induced potential toxicity. While not wishing to be bound by any particular theory, it is anticipated that the circulating antigen-presenting cells (APCs), such as dendritic cells, in the periphery are less likely to be activated by antibodies requiring cross-linking for their agonism, as the antibodies need to reach tissues for significant higher order multimerization to occur via FcγR cross linking to result in subsequent APCs activation.

Exemplary antibodies requiring cross-linking for their agonistic activity are antibodies ADC-1013 and C40M126 as described herein.

In some embodiments, the agonistic antibody or the antigen-binding fragment thereof that specifically binds CD40 activates dendritic cells (DCs) to a higher degree than B-cells.

The activation of APCs (for example dendritic cells) may be of greater clinical relevance than B-cell activation. CD40 agonist therapy of cancer is firmly linked to T-cell activation (FRENCH et al., 1999, *Nature Medicine*, 548-553; van KOOTEN et al., 2000, *J Leucoc Biol*, 67:2-17; SOTO-MAYOR et al., 1999, *Nature Medicine*, 5:780-787), and this T-cell activation depends on activation of professional antigen presenting cells, in particular, dendritic cells (MELIEF et al., 2000, *Adv Immunol*, 75: 235-282). Therefore, agonistic antibodies that specifically bind CD40 that activate DCs to a higher degree than B-cells in cross-linking dependent manner may exhibit improved efficacy and safety profile in patients.

For example, CP-870,893, a cross-linking independent agonistic CD40 antibody is about 20-fold more potent in activating B cells than dendritic cells. This superagonistic activity coupled with preferential activation of B cells may lead to cytokine release syndrome (CRS) induced by IL-6 secreted by B cells. In patient clinical trials, the most common side effects from this antibody was moderate CRS, characterized by chills, fevers, rigors and other symptoms on the day of antibody intravenous infusion. The effect of CP-870,893 on B cells may thus result in dose-limiting toxicity at a treatment dose which is insufficient to activate APCs.

In some embodiments, the agonistic antibody or the antigen-binding fragment thereof binds CD40 within CD40 residues 24-59 of SEQ ID NO: 1.

An exemplary such antibody is the antibody ADC-1013. ADC-1013 comprises the HCDR1, the HCDR2, the HCDR3, the LCDR1, the LCDR2, the LCDR3, the VH, the VL, the HC and the LC of SEQ ID NOs: 2, 3, 4, 5, 6, 7, 8, 9, 10 and 11, respectively).

Other exemplary antibodies that bind CD40 within CD40 residues 24-59 of SEQ ID NO: 1 are variants of ADC-1013, such as antibodies A4, A5, C4 and B11 described in U.S. Pat. Publ. No. 2014/0348836.

A4 comprises the HCDR1, the HCDR2, the HCDR3, the LCDR1, the LCDR2, the LCDR3, the VH, and the VL of SEQ ID NOs: 2, 3, 4, 13, 6, 20, 8 and 27, respectively and may be an IgG1 isotype.

A5 comprises the HCDR1, the HCDR2, the HCDR3, the LCDR1, the LCDR2, the LCDR3, the VH, and the VL of SEQ ID NOs: 2, 3, 4, 14, 18, 21, 8 and 28, respectively and may be an IgG1 isotype.

C4 comprises the HCDR1, the HCDR2, the HCDR3, the LCDR1, the LCDR2, the LCDR3, the VH, and the VL of SEQ ID NOs: 2, 12, 4, 13, 6, 20, 26 and 27, respectively and may be an IgG1 isotype.

B11 comprises the HCDR1, the HCDR2, the HCDR3, the LCDR1, the LCDR2, the LCDR3, the VH, and the VL of SEQ ID NOs: 2, 3, 4, 5, 6, 25, 8 and 33, respectively and may be an IgG1 isotype.

In some embodiments, the agonistic antibody or the antigen-binding fragment thereof that specifically binds CD40 comprises a heavy chain variable region 1 (HCDR1), a HCDR2, a HCDR3, a light chain variable region 1 (LCDR1), a LCDR2 and a LCDR3 of SEQ ID NOs: 2, 3, 4, 5, 6 and 7, respectively.

In some embodiments, the antibody comprises a heavy chain variable region (VH) of SEQ ID NO: 8 and a light chain variable region (VL) of SEQ ID NO: 9.

In some embodiments, the antibody comprises a heavy chain (HC) and a light chain (LC) of SEQ ID NOs: 10 and 11, respectively.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 2, 3, 4, 13, 6 and 20, respectively.

In some embodiments, the antibody comprises the VH of SEQ ID NO: 8 and the VL of SEQ ID NO: 27.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 2, 3, 4, 14, 18 and 21, respectively.

In some embodiments, the antibody comprises the VH of SEQ ID NO: 8 and the VL of SEQ ID NO: 28.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 2, 12, 4, 13, 6 and 20, respectively.

In some embodiments, the antibody comprises the VH of SEQ ID NO: 26 and the VL of SEQ ID NO: 27.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 2, 3, 4, 5, 6 and 25, respectively.

In some embodiments, the antibody comprises the VH of SEQ ID NO: 8 and the VL of SEQ ID NO: 33.

In some embodiments, the agonistic antibody or the antigen-binding fragment thereof binds CD40 within CD40 residues 46-64 and 75-76 of SEQ ID NO: 1.

An exemplary such antibody is an antibody M126. M126 comprises the HCDR1, the HCDR2, the HCDR3, the LCDR1, the LCDR2, the LCDR3, the VH, the VL, the HC and the LC of SEQ ID NOs: 34, 35, 36, 37, 38, 39, 40, 41, 48 and 49, respectively.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 34, 35, 36, 37, 38 and 39, respectively.

In some embodiments, the antibody comprises the VH and the VL of SEQ ID NOs: 40 and 41, respectively.

In some embodiments, the antibody comprises the HC and the LC of SEQ ID NOs: 48 and 49, respectively.

Additional exemplary agonistic antibodies or antigen binding fragment thereof that specifically bind CD40 that may be used in the methods of invention are antibodies G4, F6, F9 and H12 described in U.S. Pat. Publ No. 2014/0348836 and antibodies C40M9, CP-870,893 and APX-005.

G4 comprises the HCDR1, the HCDR2, the HCDR3, the LCDR1, the LCDR2, the LCDR3, the VH and the VL of SEQ ID NOs: 2, 3, 4, 15, 6, 22, 8 and 29, respectively, and may be an IgG1 isotype.

F6 comprises the HCDR1, the HCDR2, the HCDR3, the LCDR1, the LCDR2, the LCDR3, the VH and the VL of SEQ ID NOs: 2, 3, 4, 16, 19, 23, 8 and 30, respectively, and may be an IgG1 isotype.

F9 comprises the HCDR1, the HCDR2, the HCDR3, the LCDR1, the LCDR2, the LCDR3, the VH and the VL of SEQ ID NOs: 2, 3, 4, 17, 6, 24, 8 and 31, respectively, and may be an IgG1 isotype.

H12 comprises the HCDR1, the HCDR2, the HCDR3, the LCDR1, the LCDR2, the LCDR3, the VH and the VL of SEQ ID NOs: 2, 3, 4, 5, 6, 20, 8 and 32, respectively, and may be an IgG1 isotype.

C40M9 comprises the VH and the VL of SEQ ID NOs: 42 and 43, respectively, and may be an IgG1 isotype.

CP-870-893 comprises the VH and the VL of SEQ ID NOs: 44 and 45, respectively, and may be an IgG2 isotype.

APX-005 comprises the VH and the VL of SEQ ID NOs: 46 and 47, respectively, and may be an IgG1 isotype.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 2, 3, 4, 15, 6 and 22, respectively.

In some embodiments, the antibody comprises the VH of SEQ ID NO: 8 and the VL of SEQ ID NO: 29.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 2, 3, 4, 16, 19 and 23, respectively.

In some embodiments, the antibody comprises the VH of SEQ ID NO: 8 and the VL of SEQ ID NO: 30.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 2, 3, 4, 17, 6 and 24, respectively.

In some embodiments, the antibody comprises the VH of SEQ ID NO: 8 and the VL of SEQ ID NO: 31.

In some embodiments, the agonistic antibody or the antigen binding fragment thereof that specifically binds CD40 comprises the HCDR1, the HCDR2, the HCDR3, the LCDR1, the LCDR2 and the LCDR3 of SEQ ID NOs: 2, 3, 4, 5, 6 and 20, respectively.

In some embodiments, the antibody comprises the VH of SEQ ID NO: 8 and the VL of SEQ ID NO: 32.

In some embodiments, the agonistic antibody or the antigen binding fragment thereof that specifically binds CD40 comprises the VH and the VL of SEQ ID NOs: 42 and 43, respectively.

In some embodiments, the agonistic antibody or the antigen binding fragment thereof that specifically binds CD40 comprises the VH and the VL of SEQ ID NOs: 44 and 45, respectively.

In some embodiments, the agonistic antibody or the antigen binding fragment thereof that specifically binds CD40 comprises the VH and the VL of SEQ ID NOs: 46 and 47, respectively.

In some embodiments, the agonistic antibody or the antigen-binding fragment thereof that specifically binds CD40 is humanized. In some embodiments, the antibody is human.

In some embodiments the agonistic antibody or the antigen-binding fragment thereof that specifically binds CD40 is an IgG1 isotype. In some embodiments the agonistic antibody or the antigen-binding fragment thereof that specifically binds CD40 is an IgG2 isotype. In some embodiments the agonistic antibody or the antigen-binding fragment thereof that specifically binds CD40 is an IgG3 isotype. In some embodiments the agonistic antibody or the antigen-binding fragment thereof that specifically binds CD40 is an IgG4 isotype.

In some embodiments, the agonistic antibody or the antigen-binding fragment thereof that specifically binds CD40 comprises at least one mutation in an Fc region that enhances binding of the antibody to FcγRIIb.

As used herein, unless otherwise noted, the term "enhanced binding to FcγRIIb" refers to a statistically significant increase in binding (e.g. decrease in $EC_{50}$ value) to FcγRIIb by the CD40 antibody comprising at least one mutation in the Fc region when compared to the same antibody without the mutation.

Binding of the antibody to FcγRIIb may be assessed on cells engineered to express FcγRIIb using flow cytometry. In an exemplary binding assay, $2\times10^5$ cells per well are seeded in 96-well plate and blocked in BSA Stain Buffer (BD Biosciences, San Jose, USA) for 30 min at 4° C. Cells are incubated with a test antibody on ice for 1.5 hour at 4° C. After being washed twice with BSA stain buffer, the cells are incubated with R-PE labeled anti-human IgG secondary antibody (Jackson Immunoresearch Laboratories) for 45 min at 4° C. The cells are washed twice in stain buffer and then re-suspended in 150 µL of Stain Buffer containing 1:200 diluted DRAQ7 live/dead stain (Cell Signaling Technology, Danvers, USA). PE and DRAQ7 signals of the stained cells are detected by Miltenyi MACSQuant flow cytometer (Miltenyi Biotec, Auburn, USA) using B2 and B4 channel respectively. Live cells are gated on DRAQ7 exclusion and the geometric mean fluorescence signals are determined for at least 10,000 live events collected. FlowJo software (Tree Star) is used for analysis. Data is plotted as the logarithm of antibody concentration versus mean fluorescence signals. Nonlinear regression analysis is performed by GraphPad Prism 6 (GraphPad Software, Inc.) and EC50 values are calculated.

Enhanced binding of the agonistic antibody or the antigen-binding fragment thereof that specifically binds CD40 to FcγRIIb may enhance crosslinking of CD40 molecules leading to stronger CD40 activation. Exemplary Fc mutations that result in antibodies having increased FcγRIIb are a S267E mutation, a S267D mutation, a S267E/I332E mutation, a S267E/L328F mutation, a G236D/S267E mutation and an E233D/G237D/H268D/P271G/A330R/P238D mutation, residue numbering according to the EU Index.

In some embodiments, the agonistic antibody or the antigen-binding fragment thereof that specifically binds CD40 is an IgG1 isotype comprising a S267E mutation when compared to the wild-type IgG1.

In some embodiments, the agonistic antibody or the antigen-binding fragment thereof that specifically binds CD40 is an IgG1 isotype comprising a S267E/I332E mutation when compared to the wild-type IgG1.

In some embodiments, the agonistic antibody or the antigen-binding fragment thereof that specifically binds CD40 is an IgG1 isotype comprising a S267E/L328F mutation when compared to the wild-type IgG1.

In some embodiments, the agonistic antibody or the antigen-binding fragment thereof that specifically binds CD40 is an IgG1 isotype comprising a E233D/G237D/H268D/P271G/A330R/P238D mutation when compared to the wild-type IgG1.

As used herein in relation to description of antibodies, the term "within" shall mean that 80% or more of the epitope residues the antibody binds to residues within the recited amino acid stretches (e.g. for example 80% or more epitope residues bind within amino acid stretches 24-59 of SEQ ID NO: 1 and that up to 20% of the epitope residues the antibody binds to reside outside of the recited amino acid stretches 24-59 of SEQ ID NO: 1.

The CD40 epitope the antibody binds to may be resolved for example using hydrogen/deuterium exchange (H/D exchange) or by analyzing a crystal structure of the antibody in complex with CD40. The epitope residues are those which are protected by the antibody by at least 5% difference in deuteration levels through H/D exchange or those surface exposed amino acid residues determined to bind the antibody in a crystal structure of a complex of the antibody and CD40. In the crystal structure of a complex of the antibody and CD40, the epitope residues are those CD40 residues that reside within 4 Å distance or less from any of the antibody CDR residues.

In an H/D exchange assay, CD40 protein is incubated in the presence or absence of the antibody in deuterated water for predetermined times resulting in deuterium incorporation at exchangeable hydrogen atoms which are unprotected by the antibody, followed by protease digestion of the protein and analyses of the peptide fragments using LC-MS. In an exemplary assay, 5 µL of the test antibody (10 µg) or 5 µL of the complex of CD40 and the test antibody (10 & 7.35 µg, respectively) is incubated with 120 µL deuterium oxide labeling buffer (50 mM phosphate, 100 mM sodium chloride at pH 7.4) for 0 sec, 60 sec, 300 sec, 1800 sec, 7200 sec, and 14400 sec. Deuterium exchange is quenched by adding 63 µL of 5 M guanidine hydrochloride and final pH is 2.5. The quenched sample is subjected to on-column pepsin/protease type XIII digestion and LC-MS analysis. For pepsin/protease type XIII digestion, 5 µg of the samples in 125 µL control buffer (50 mM phosphate, 100 mM sodium chloride at pH 7.4) are denatured by adding 63 µL of 5 M guanidine hydrochloride (final pH is 2.5) and incubating the mixture for 3 min. Then, the mixture is subjected to on-column pepsin/protease type XIII digestion and the resultant peptides analyzed using an UPLC-MS system comprised of a Waters Acquity UPLC coupled to a Q Exactive™ Hybrid Quadrupole-Orbitrap Mass Spectrometer (Thermo). Raw MS data is processed using HDX WorkBench, software for the analysis of H/D exchange MS data. The deuterium levels are calculated using the average mass difference between the deuteriated peptide and its native form (to). Peptide identification is done through searching MS/MS data against the CD40 sequence with Mascot. The mass tolerance for the precursor and product ions is 20 ppm and 0.05 Da, respectively.

For X-ray crystallography, CD40 and the test antibody are expressed and purified using standard protocols. The CD40/test antibody complex is incubated overnight at 4° C., concentrated, and separated from the uncomplexed species using size-exclusion chromatography. The complex is crystallized by the vapor-diffusion method from various known test solutions for example solutions containing PEG3350, ammonium citrate and 2-(N-Morpholino)ethanesulfonic acid (MES).

Antibodies binding within human CD40 residues 24-59 of SEQ ID NO: 1 may be generated by isolating antibodies binding CD40 using phage display libraries, selecting those antibodies that compete with the reference antibody ADC-1013 (VH of SEQ ID NO: 8 and VL of SEQ ID NO: 9) for binding to CD40 by 100%, and confirming the epitope of the generated antibodies by solving the crystal structure of the antibody/CD40 complex. Alternatively, mice, rats or rabbits may be immunized using peptides encompassing residues 24-59 of SEQ ID NO: 1 and the generated antibodies may be evaluated for their binding within the recited region.

The present invention further provides a method of treating cancer, preferably a solid tumor or hematological malignancy, comprising administering to a subject in need thereof a therapeutically effective amount of co-therapy or combination therapy comprising, consisting or consisting essentially of (a) a small molecule inhibitor of CSF-1R of formula (I)

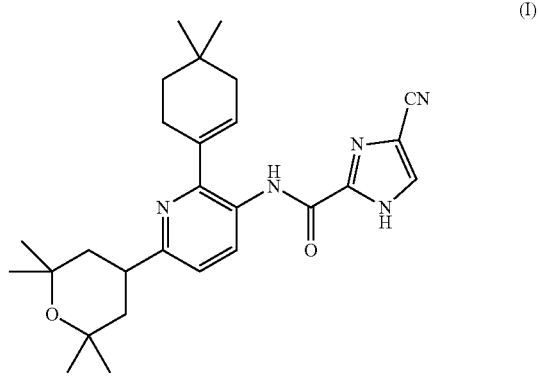 [SMILES: CC1(C)CC=C(c2nc(C3CC(C)(C)OC(C)(C)C3)ccc2NC(=O)c2nc(C#N)c[nH]2)CC1]

and (b) an agonistic antibody or an antigen-binding fragment thereof that specifically binds CD40 comprising the HCDR1, the HCDR2, the HCDR3, the LCDR1, the LCDR2 and the LCDR3 of SEQ ID NOs: 2, 3, 4, 5, 6 and 7, respectively.

In some embodiments, the antibody or the antigen-binding fragment thereof comprises the VH of SEQ ID NO: 8 and the VL of SEQ ID NO: 9.

In some embodiments, the antibody comprises a heavy chain of SEQ ID NO: 10 and a light chain of SEQ ID NO: 11.

The present invention further provides a method of treating cancer, preferably a solid tumor or hematological malignancy, comprising administering to a subject in need thereof a therapeutically effective amount of co-therapy or combination therapy comprising, consisting or consisting essentially of (a) a small molecule inhibitor of CSF-1R of formula (I)

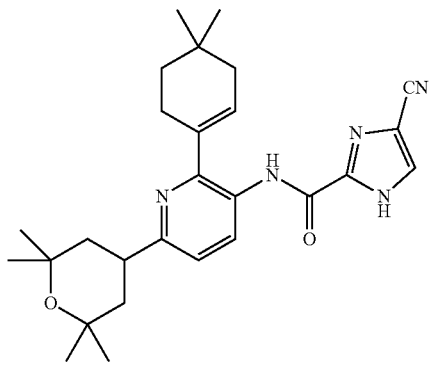

and (b) an agonistic antibody or an antigen-binding fragment thereof that specifically binds CD40 comprising the HCDR1, the HCDR2, the HCDR3, the LCDR1, the LCDR2 and the LCDR3 of SEQ ID NOs: 34, 35, 36, 37, 38 and 39, respectively.

In some embodiments, the antibody or the antigen-binding fragment thereof comprises the VH of SEQ ID NO: 40 and the VL of SEQ ID NO: 41.

In some embodiments, the antibody comprises the heavy chain of SEQ ID NO: 48 and the light chain of SEQ ID NO: 49.

The present invention further provides a method of treating cancer, preferably a solid tumor or hematological malignancy, comprising administering to a subject in need thereof a therapeutically effective amount of co-therapy or combination therapy comprising, consisting or consisting essentially of (a) a small molecule inhibitor of CSF-1R of formula (I)

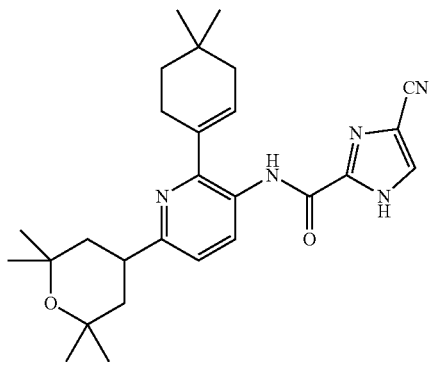

and (b) an agonistic antibody or an antigen-binding fragment thereof that specifically binds CD40 comprising the HCDR1, the HCDR2, the HCDR3, the LCDR1, the LCDR2 and the LCDR3 of SEQ ID NOs:
2, 3, 4, 13, 6 and 20, respectively;
2, 3, 4, 14, 18 and 21, respectively;
2, 12, 4, 13, 6 and 20, respectively;
2, 3, 4, 15, 6 and 22, respectively;
2, 3, 4, 16, 19 and 23, respectively;
2, 3, 4, 17, 6 and 24, respectively;
2, 3, 4, 5, 6 and 20, respectively; or
2, 3, 4, 5, 6 and 25, respectively.

In some embodiments, the antibody or the antigen-binding fragment thereof comprises the VH and the VL of SEQ ID NOs:
8 and 27, respectively;
8 and 28, respectively;
26 and 27, respectively;
8 and 29, respectively;
8 and 30, respectively;
8 and 31, respectively;
8 and 32, respectively; or
8 and 33, respectively.

The present invention further provides a method of treating cancer, preferably a solid tumor or hematological malignancy, comprising administering to a subject in need thereof a therapeutically effective amount of co-therapy or combination therapy comprising, consisting or consisting essentially of (a) a small molecule inhibitor of CSF-1R of formula (I)

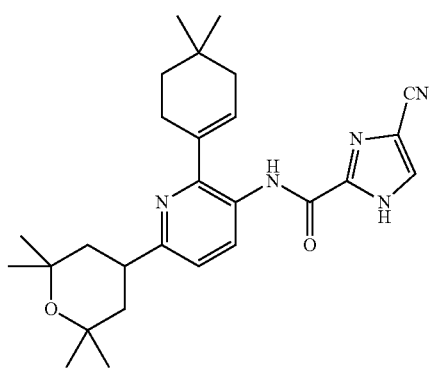

and (b) an agonistic antibody or the antigen-binding fragment thereof that specifically binds CD40 comprising the VH of SEQ ID NO: 42 and the VL of SEQ ID NO: 43.

The present invention further provides a method of treating cancer, preferably a solid tumor or hematological malignancy, comprising administering to a subject in need thereof a therapeutically effective amount of co-therapy or combination therapy comprising, consisting or consisting essentially of (a) a small molecule inhibitor of CSF-1R of formula (I)

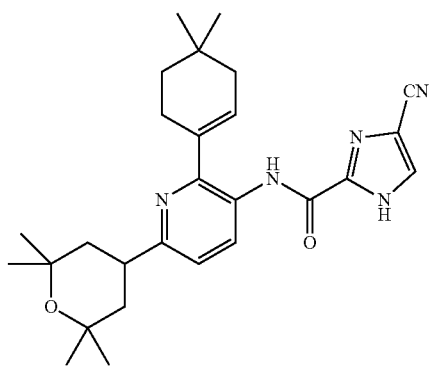

and (b) an agonistic antibody or an antigen-binding fragment thereof that specifically binds CD40 comprising the VH of SEQ ID NO: 44 and the VL of SEQ ID NO: 45.

The present invention further provides a method of treating cancer, preferably a solid tumor or hematological malignancy, comprising administering to a subject in need thereof a therapeutically effective amount of co-therapy or combination therapy comprising, consisting or consisting essentially of (a) a small molecule inhibitor of CSF-1R of formula (I)

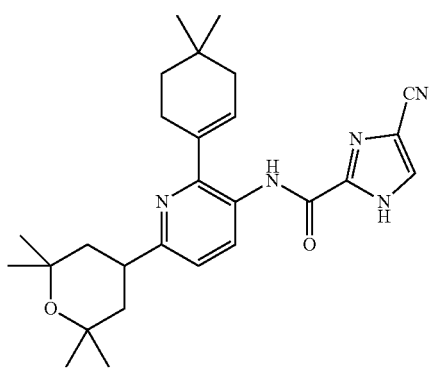

and (b) an agonistic antibody or an antigen-binding fragment thereof that specifically binds CD40 comprising the VH of SEQ ID NO: 46 and the VL of SEQ ID NO: 47.

In certain embodiments of the present invention, the cancer is a solid tumor or hematological malignancy. In certain embodiments of the present invention, the cancer is a solid tumor. In certain embodiments of the present invention, the cancer is a hematological malignancy. In certain embodiment of the present invention, the cancer is selected from the group consisting of pancreatic cancer, prostate cancer (including but not limited to castration-resistant prostate cancer), colorectal cancer and lung cancer (including but not limited to, non-small cell lung cancer). In certain embodiments of the present invention, the cancer is selected from the group consisting of melanoma and non-Hodgkin's lymphoma.

In certain embodiments of the present invention, the solid tumor is a pancreatic cancer. In certain embodiments of the present invention, the solid tumor is a colorectal cancer. In certain embodiments of the present invention, the solid tumor is a lung cancer. In certain embodiments of the present invention, the solid tumor is a prostate cancer. In certain embodiments of the present invention, the solid tumor is a breast cancer. In certain embodiments of the present invention, the solid tumor is a melanoma. In certain embodiments of the present invention, the lung cancer is non-small cell lung cancer (NSCLC). In some embodiments, the prostate cancer is castration-resistant prostate cancer. In certain embodiments of the present invention, the cancer is a hematological malignancy. In certain embodiments of the present invention, the hematological malignancy is non-Hodgkin's lymphoma.

In certain embodiments of the present invention, the small molecule CSF-1R inhibitor and the agonistic antibody or the antigen-binding fragment thereof that specifically binds CD40 are administered simultaneously, sequentially or separately.

In certain embodiments of the present invention, the small molecule CSF-1R inhibitor is administered prior to administration of the agonistic antibody or the antigen-binding fragment thereof that specifically binds CD40. In certain embodiments of the present invention, the small molecule CSF-1R inhibitor is administered for between 1 and 30 days, or any number of days or range of days thereof, prior to administration of the agonistic antibody or the antigen-binding fragment thereof that specifically binds CD40. In certain embodiments of the present invention, the small molecule CSF-1R inhibitor is administered for between 3 and 21 days prior to administration of the agonistic antibody or the antigen-binding fragment thereof that specifically binds CD40. In certain embodiments of the present invention, the small molecule CSF-1R inhibitor is administered for between 7 and 14 days prior to administration of the agonistic antibody or the antigen-binding fragment thereof that specifically binds CD40.

In certain embodiments of the present invention, the small molecule CSF-1R inhibitor is administered once daily, in an amount of between about 50 mg per day to about 600 mg per day, or any amount or range therein (preferably in an amount of between about 100 mg per day and about 250 mg per day) for between about 7 and about 14 days, or any number of days or range of days therein, prior to administration of the agonistic antibody or the antigen-binding fragment thereof that specifically binds CD40.

In certain embodiments of the present invention, the small molecule CSF-1R inhibitor is administered for between 1 and 30 days, or any number of days or range of days therein, (preferably between 3 and 21 days, more preferably between 7 and 14 days) prior to administration of the agonistic antibody or the antigen-binding fragment thereof that specifically binds CD40, and then further administered concurrently with administration of the agonistic antibody. Thus for example, the CSF-1R small molecule inhibitor may be administered for 7 days, followed by administration of both the CSF-1R small molecule inhibitor and the agonistic antibody or the antigen-binding fragment thereof that specifically binds CD40 for any period of time thereafter. Further, the period of co-administration of the CSF-1R small molecule and the agonistic antibody or the antigen-binding fragment thereof that specifically binds CD40 may encompass the full period of treatment with the agonistic antibody or the antigen-binding fragment thereof that specifically binds CD40 or any portion of the period of treatment with the agonistic antibody or the antigen-binding fragment thereof that specifically binds CD40 (including alternating administration wherein for one or more days both the CSF-1R small molecule and the agonistic antibody or the antigen-binding fragment thereof that specifically binds CD40 are administered, followed by one or more days of administration of the small molecule CSF-1R inhibitor or the agonistic antibody or the antigen-binding fragment thereof that specifically binds CD40).

In certain embodiments of the present invention, the small molecule CSF-1R inhibitor is administered concurrently with administration of the agonistic antibody or the antigen-binding fragment thereof that specifically binds CD40. In certain embodiments, the small molecule CSF-1R inhibitor and the agonistic antibody or the antigen-binding fragment thereof that specifically binds CD40 are each administered daily or weekly. One skilled in the art will recognize that wherein the small molecule CSF-1R inhibitor and the agonistic antibody or the antigen-binding fragment thereof that specifically binds CD40 are administered concurrently, both compounds do not need to be administered at the same time, but may be both administered on the same day, with a delay between administration of the small molecule CSF-1R inhibitor and the agonistic antibody or the antigen-binding fragment thereof that specifically binds CD40 of minutes or hours, not exceeding 24 hours, for example, 24 hours, 20 hours, 18 hours, 16 hours, 14 hours, 12 hours, 10 hours, 8 hours, 6 hours, 4 hours, 2 hours, 1 hours, 30 min or 15 min.

One skilled in the art will recognize that wherein the small molecule CSF-1R inhibitor and the agonistic antibody or the antigen-binding fragment thereof that specifically binds CD40 are administered concurrently, and the dosing regimens for the small molecule CSF-1R inhibitor and the agonistic antibody or the antigen-binding fragment thereof that specifically binds CD40 are not the same (for example, the small molecule CSF-1R inhibitor is administered daily and the agonistic antibody or the antigen-binding fragment thereof that specifically binds CD40 is administered weekly or monthly), the term "concurrently" shall include an administration regimen wherein the small molecule CSF-1R inhibitor and the agonistic antibody or the antigen-binding fragment thereof that specifically binds CD40 are administered concurrently on those occasions (e.g. days) when both therapeutic agents of the combination therapy or co-therapy are administered, irrespective of whether or not there are other administration occasions (e.g. days) on which only one of the agents of the combination therapy or co-therapy is administered.

In certain embodiments of the present invention the agonistic antibody or the antigen-binding fragment thereof that specifically binds CD40 is administered prior to administration of the small molecule CSF-1R inhibitor.

In certain embodiments of the present invention, the agonistic antibody or the antigen-binding fragment thereof that specifically binds CD40 is administered for between 1 and 30 days, or any number of days or range of days therein, prior to administration of the small molecule CSF-1R inhibitor. In certain embodiments of the present invention, the agonistic antibody or the antigen-binding fragment thereof that specifically binds CD40 is administered for between 1 and 21 days prior to administration of small molecule CSF-1R inhibitor. In certain embodiments of the present invention, the agonistic antibody or the antigen-binding fragment thereof that specifically binds CD40 is administered for between 1 and 14 days prior to administration of the small molecule CSF-1R inhibitor.

In certain embodiments of the present invention, the agonistic antibody or the antigen-binding fragment thereof that specifically binds CD40 is administered once daily, once weekly or once biweekly, in an amount of between about 0.25 mg/kg to about 100 mg/kg, or any amount or range therein (preferably in an amount of between about 1 mg/kg to about 20 mg/kg), for between 1 and 30 days, prior to administration of the small molecule CSF-1R inhibitor.

In certain embodiments of the present invention, the agonistic antibody or the antigen-binding fragment thereof that specifically binds CD40 is administered for between 1 day and 30 days (preferably between 1 and 14 days, more preferably between 1 and 7 days) prior to administration of the small molecule CSF-1R inhibitor, and then further administered concurrently with administration of the small molecule CSF-1R inhibitor. Thus for example, the agonistic antibody or the antigen-binding fragment thereof that specifically binds CD40 may be administered once daily or once weekly over a period of 1 to 7 days, followed by administration of both the CSF-1R small molecule inhibitor and the agonistic antibody or the antigen-binding fragment thereof that specifically binds CD40 for any period of time thereafter. Further, the period of co-administration of the agonistic antibody or the antigen-binding fragment thereof that specifically binds CD40 and the small molecule CSF-1R inhibitor may encompass the full period of treatment with the small molecule CSF-1R inhibitor or any portion of the period of treatment with the small molecule CSF-1R inhibitor (including alternating administration wherein for one or more days both the agonistic antibody or the antigen-binding fragment thereof that specifically binds CD40 and the CSF-1R small molecule are administered, followed by one or more days of administration of only the CSF-1R small molecule or only the agonistic antibody or the antigen-binding fragment thereof that specifically binds CD40).

In certain embodiments, the agonistic antibody or the antigen-binding fragment thereof that specifically binds CD40 is administered in an amount in the range of from about 0.25 mg/kg to about 100 mg/kg, such as from about 0.25 mg to about 50 mg/kg, or any amount or range therein, preferably in an amount in the range of from about 0.5 mg/kg to about 30 mg/kg, more preferably in an amount in the range of from about 1 mg/kg to about 20 mg/kg. For example, the agonistic antibody or the antigen-binding fragment thereof that specifically binds CD40 may be administered in amount of about 0.25 mg/kg, 0.5 mg/kg, 1 mg/kg, 2 mg/kg, 2.5 mg/kg, 3 mg/kg, 4 mg/kg, 5 mg/kg, 6 mg/kg, 7.5 mg/kg, 8 mg/kg, 10 mg/kg, 12 mg/kg, 15 mg/kg, 16 mg/kg, 20 mg/kg, 25 mg/kg, 30 mg/kg, 40 mg/kg, 50 mg/kg, 60 mg/kg, 70 mg/kg, 80 mg/kg, 90 mg/kg or 100 mg/kg.

In certain embodiments, the agonistic antibody or the antigen-binding fragment thereof that specifically binds CD40 is administered every other day, every third day, every fifth day, once a week, once every two weeks, once every three weeks, once every four weeks, once a month, once every two months or once every three months.

In certain embodiments, the agonistic antibody or the antigen-binding fragment thereof that specifically binds CD40 is administered between about once a week and about once every three months, in an amount in the range of from about 1 mg/kg to about 100 mg/kg.

In certain embodiments, the agonistic antibody or the antigen-binding fragment thereof that specifically binds CD40 is administered once a week or once a month in an amount in the range of from about 1 mg/kg to about 50 mg/kg.

In certain embodiments, the agonistic antibody or the antigen-binding fragment thereof that specifically binds CD40 is administered once a week in an amount in the range of from about 1 mg/kg to about 10 mg/kg.

In certain embodiments, the present invention is directed to methods of treating cancer (preferably a solid tumor or hematological malignancy) in a subject in need thereof, wherein the subject is a patient having a CSF-1R expressing tumor or a tumor with CSF-1R expressing macrophage infiltrate, wherein the tumor overexpresses CSF-1R ligand.

In certain embodiments of the present invention, the subject is resistant or refractory to treatment with a CSF-1R inhibitor (including, but not limited to a small molecule CSF-1R inhibitor or a CSF-1R antibody). In certain embodiments of the present invention, the subject is resistant or refractory to treatment with a CD40 agonist (including but not limited to an agonistic antibody that specifically binds CD40).

Various qualitative and/or quantitative methods may be used to determine if a subject is resistant or refractory to treatment. Symptoms that may be associated with resistance to a CSF-1R inhibitor or an agonistic antibody that specifically binds CD40 include, for example, a decline or plateau of the well-being of the patient, an increase in the size of a tumor, arrested or slowed decline in growth of a tumor, and/or the spread of cancerous cells in the body from one location to other organs, tissues or cells. Re-establishment or worsening of various symptoms associated with cancer may also be an indication that a subject has developed or is susceptible to developing resistance, such as anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with lung cancer may include persistent cough, coughing up blood, shortness of breath, wheezing chest pain, loss of appetite, losing weight without trying and fatigue. One skilled in oncology may readily identify symptoms associated with a particular cancer type.

The present invention further provides for a method of treating a cancer, comprising administering to a subject in need thereof a therapeutically effective amount of co-therapy or combination treatment comprising, consisting or consisting essentially of (a) a small molecule CSF-1R inhibitor and (b) an agonistic antibody or an antigen-binding fragment thereof that specifically binds CD40, and further comprising administration of radiation therapy.

The present invention further provides for a method of treating a cancer, comprising administering to a subject in need thereof a therapeutically effective amount of co-therapy or combination treatment comprising, consisting or consisting essentially of (a) a small molecule CSF-1R inhibitor and (b) an agonistic antibody or an antigen-binding fragment thereof that specifically binds CD40, and further comprises administration of at least one additional therapeutic agent. In certain embodiments of the present invention, the at least one additional therapeutic agent is a standard-of-care treatment for cancer.

In certain embodiments of the present invention, the at least one additional therapeutic agent may be one or more of the chemotherapeutic drugs or other anti-cancer therapeutics known to those of skill in the art. Chemotherapeutic agents are chemical compounds useful in the treatment of cancer and include growth inhibitory agents or other cytotoxic agents and include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and cyclosphosphamide (CY-TOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL®docetaxel (TAXOTERE®) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including sorafenib (NEXAVAR®), sunitinib (SUTENT®), pazopanib (VOTRIENT™), toceranib (PALLADIA™), vandetanib (ZACTIMA™), cediranib (RECENTIN®), regorafenib (BAY 73-4506), axitinib (AG013736), lestaurtinib (CEP-701), erlotinib (TARCEVA®), gefitinib (IRESSA™), BIBW 2992 (TOVOK™), lapatinib (TYKERB®), neratinib (HKI-272), and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in *Medical Oncology* (Calabresi et aL, eds.), Chapter 10, McMillan Publishing, are also applicable to the methods of the present invention.

Exemplary at least one additional therapeutic agents include tyrosine kinase inhibitors and targeted anti-cancer therapies such as Iressa® (gefitinib) and Tarceva (erlotinib) and other antagonists of HER2, HER3, HER4 or VEGF. Exemplary HER2 antagonists include CP-724-714, HERCEPTIN™ (trastuzumab), OMNITARG™ (pertuzumab), TAK-165, lapatinib (EGFR and HER2 inhibitor), and GW-282974. Exemplary HER3 antagonists include anti-Her3 antibodies (see e.g., U.S. Pat. Publ. No. US2004/0197332). Exemplary HER4 antagonists include anti-HER4 siRNAs (see e.g., Maatta et al., Mol Biol Cell 17: 67-79, 2006. An exemplary VEGF antagonist is Bevacizumab (Avastin™).

In certain embodiments of the present invention, wherein the cancer to be treated is pancreatic cancer, the at least one additional therapeutic agent is albumin-bound paclitaxel (ABRAXANE®), gemcitabine (Gemzar®) and fluorouracil (5-FU), or a combination of (5-FU/leucovorin, irinotecan, and oxaliplatin.

In certain embodiments of the present invention, wherein the cancer to be treated is prostate cancer (including but not limited to castration-resistant prostate cancer), the at least one additional therapeutic agent is abiraterone acetate (Zytiga®), bicalutamide (Casodex®), cabazitaxel (Jevtana®), conjugated estrogens (Premarin®), stradiol (Estrace®), estradiol valerate (Delestrogen®), estrogens, esterified (Menest®), degarelix (Firmagon®), docetaxel (Taxotere®), enzalutamide (Xtandi®), flutamide, goserelin acetate (Zoladex®), Cabazitaxel (Jevtana®), leuprolide acetate (Lupron®), mitoxantrone hydrochloride, nilutamide (Nilandron®) Sipuleucel-T (Provenge®) and radium 223 dichloride (Xofigo®).

In certain embodiments of the present invention, wherein the cancer to be treated is lung cancer, for example NSCLC, the at least one additional therapeutic agent is methotrexate (Folex®, Mexate®), paclitaxel (Abraxane®), afatinib (Gilotrif®), everolimus (Afinitor®), alectinib (Alecensa®), pemetrexed disodium (Alimta®), bevacizumab (Avastin®), carboplatin, ceritinib (Zykadia®), crizotinib (Xalkori®), ramucirumab (Cyramza®), docetaxel, everolimus (Afinitor®), gefitinib (Iressa®), afatinib dimaleate (Gilotrif®), gemcitabine hydrochloride (Gmezar®), pembrolizumab (Keytruda®), mechlorethamine hydrochloride (Mustargen®), vinorelbine tartrate (Navelbine®), necitumumab (Portrazza®), nivolumab (Opdivo®), osimertinib, paclitaxel (Taxol®), carboplatin, pemetrexed disodium, ramucirumab (Cyramza®) and osimertinib (Tagrisso®).

In certain embodiments of the present invention, wherein the cancer to be treated is renal cell carcinoma, the additional therapeutic agent(s) are selected from the group consisting of everolimus (Afinitor®), aldesleukin, bevacizumab (Avastin®), axitinib (Inlyta®), cabozantinib-S-Malate (Cabometyx®), aldesleukin (Proleukin®), lenvatinib mesylate (Lenvima®), sorafenib tosylate (Nexavar®), nivolumab (Opdivo®), pazopanib hydrochloride, sorafenib tosylate, sunitinib (Sutent®), temsirolimus (Torisel®) and pazopanib hydrochloride (Votrient®).

In certain embodiments of the present invention, wherein the cancer to be treated is colorectal cancer, the at least one additional therapeutic agent is a chemotherapy regimen of 5-fluorouracil and leucovorin (with or without a targeted drug), capecitabine (XELODA®) (with or without a targeted drug), irinotecan (CAMPTOSAR®) (with or without a targeted drug), cetuximab (ERBITUX®), panitumumab (VECTIBIX®), pegorafenib (STIVARGA®), a chemotherapy regimen of trifluridine and tiptracil (LONSURF®), FOLFOX: chemotherapy regomen of leucovorin, 5-fluorouracil and oxaliplatin (ELOXATIN®), FOLFIRI: chemotherapy regimen of leucovorin, 5-fluorouracil, and irinotecan (CAMPTOSAR®), CapeOX: chemotherapy regimen of capecitabine (XELODA®) and oxaliplatin (ELOXATIN®), FOLFOXIRI: chemotherapy regimen of leucovorin, 5-fluorouracil, oxaliplatin (ELOXATIN®), and irinotecan (CAMPTOSAR®), or any of the above individual agents or chemotherapy regiments in combination with each other or in combination with a drug that targets VEGF such as bevacizumab (AVASTIN®), ziv-aflibercept (ZALTRAP®), ramucirumab (CYRAMZA®), and the like.

In certain embodiments of the present invention, wherein the cancer to be treated is melanoma, the at least one additional therapeutic agent is Aldesleukin, cobimetinib (Cotellic®), dabrafenib (Tafinlar®), dacarbazine (DTIC-Dome®), talimogene laherparepvec (Imlygic®), ipilimumab (Yervoy®), pembrolizumab (Keytruda®), trametinib (Mekinist®), nivolumab (Opdivo®), Peginterferon Alfa-2b (PEG-Intron®, Sylatron®), recombinant interferon Alfa-2b, talimogene laherparepvec and vemurafenib (Zelboraf®).

In certain embodiments of the present invention, wherein the cancer to be treated is non-Hodgkin's lymphoma, the at least one additional therapeutic agent is an alkylating agent (such as cyclophosphamide (Cytoxan®), chlorambucil, bendamustine (Treanda®), ifosfamide (Ifex®), and the like), a corticosteroid (such as prednisone, dexamethasone (Decadron®), and the like), a platinum drug (such as cisplatin, carboplatin, oxaliplatin, and the like), a purine analog (such as fludarabine (Fludara®), pentostatin (Nipent®), cladribine (2-CdA, Leustatin®), and the like), an anti-metabolite agent (such as cytarabine (ara-C), gemcitabine (Gemzar®), methotrexate, pralatrexate (Folotyn®), and the like) or other chemotherapeutic agent (such as vincristine (Oncovin®), doxorubicin (Adriamycin®), mitoxantrone, etoposide (VP-16), bleomycin, and the like). In the treatment of non-Hodgkin's lymphoma, the at least one additional therapeutic agent may further be combined with immunotherapy, such as monoclonal antibody therapy with for example rituximab (Rituxan®).

One skilled in the art will recognize that additional standard therapies and regimens for the treatment of cancers (including solid tumors or hematological malignancies) listed herein, are known or may be determined by consulting appropriate references, such as may be drug package inserts, FDA guidelines, the American Cancer Society (e.g. https//www.cancer.org website), and like. It is intended that said additional standard therapies are included in the scope of possible "at least one additional therapeutic agent" in the methods of the present invention.

In certain embodiments, the present invention is directed to methods of treating cancer comprising administering a therapeutically effective amount of co-therapy or combination therapy comprising, consisting or consisting essentially of (a) a small molecule CSF-1R inhibitor, (b) an agonistic antibody or an antigen-binding fragment thereof that specifically binds CD40 and any form of radiation therapy including, but not limited to external beam radiation, intensity modulated radiation therapy (IMRT), focused radiation, and any form of radiosurgery including Gamma Knife, Cyberlaiife, Linac, and interstitial radiation (for example implanted radioactive seeds, GliaSite balloon), and/or with surgery.

Focused radiation methods that may be used include stereotactic radiosurgery, fractionated stereotactic radiosurgery, and intensity-modulated radiation therapy (IMRT). It is apparent that stereotactic radiosurgery involves the precise delivery of radiation to a tumorous tissue, for example, prostate cancer, while avoiding the surrounding non-tumorous, normal tissue. The dosage of radiation applied using stereotactic radiosurgery may vary typically from 1 Gy to about 30 Gy, and may encompass intermediate ranges including, for example, from 1 to 5, 10, 15, 20, 25, up to 30 Gy in dose. Because of noninvasive fixation devices, stereotactic radiation need not be delivered in a single treatment. The treatment plan may be reliably duplicated day-to-day, thereby allowing multiple fractionated doses of radiation to be delivered. When used to treat a tumor over time, the radiosurgery is referred to as "fractionated stereotactic radiosurgery" or FSR. In contrast, stereotactic radiosurgery refers to a one-session treatment. Fractionated stereotactic radiosurgery may result in a high therapeutic ratio, i.e., a high rate of killing of tumor cells and a low effect on normal tissue. The tumor and the normal tissue respond differently to high single doses of radiation vs. multiple smaller doses of radiation. Single large doses of radiation may kill more normal tissue than several smaller doses of radiation may. Accordingly, multiple smaller doses of radiation can kill more tumor cells while sparing normal tissue. The dosage of radiation applied using fractionated stereotactic radiation may vary from range from 1 Gy to about 50 Gy, and may encompass intermediate ranges including, for example, from 1 to 5, 10, 15, 20, 25, 30, 40, up to 50 Gy in hypofractionated doses. Intensity-modulated radiation therapy (IMRT) may also be used. IMRT is an advanced mode of high-precision three-dimensional conformal radiation therapy (3DCRT), which uses computer-controlled linear accelerators to deliver precise radiation doses to a malignant tumor or specific areas within the tumor, the profile of each radiation beam is shaped to fit the profile of the target from a beam's eye view (BEV) using a multileaf collimator (MLC), thereby producing a number of beams. IMRT allows the radiation dose to conform more precisely to the three-dimensional (3-D) shape of the tumor by modulating the intensity of the radiation beam in multiple small volumes. Accordingly, IMRT allows higher radiation doses to be focused to regions within the tumor while minimizing the dose to surrounding normal critical structures. IMRT improves the ability to conform the treatment volume to concave tumor shapes, for example, when the tumor is wrapped around a vulnerable structure, such as the spinal cord or a major organ or blood vessel. Suitable radiation sources for use as a cell conditioner include both solids and liquids.

The agonistic antibodies or antigen-binding fragments thereof that specifically bind CD40 may be provided in suitable pharmaceutical compositions comprising the antibody and a pharmaceutically acceptable carrier. The carrier may be diluent, adjuvant, excipient, or vehicle with which the agonistic antibodies that bind CD40 are administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (for example, filtration). The compositions may contain pharmaceutically acceptable auxiliary substances as required to approximate physiological conditions such as pH adjusting and buffering agents, stabilizing, thickening, lubricating and coloring agents, etc. The concentration of the agonistic antibodies or antigen-binding fragments thereof that specifically bind CD40 in such pharmaceutical formulation may vary widely, i.e., from less than about 0.5%, usually to at least about 1% to as much as 15 or 20%, 25%, 30%, 35%, 40%, 45% or 50% by weight and will be selected primarily based on required dose, fluid volumes, viscosities, etc., according to the particular mode of administration selected. Suitable vehicles and formulations, inclusive of other human proteins, for example, human serum albumin, are described, for example, in for example Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, see especially pp. 958-989.

The agonistic antibodies or antigen-binding fragments thereof that specifically bind human CD40 may be administered to a subject by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose given to the subject may be sometimes 0.005 mg to about 100 mg/kg, for example about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, for example, 500, 400, 300, 250, 200, or 100 mg/m$^2$. Usually between 1 and 8 doses, (for example, 1, 2, 3, 4, 5, 6, 7 or 8) may be administered, but 9, 10, 11, 12, 13, 14, 15, 16, 17, 18, 19, 20 or more doses may be given.

The administration of the agonistic antibodies or antigen-binding fragments thereof that specifically bind CD40 may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

The agonistic antibodies or antigen-binding fragments thereof that specifically bind CD40 may be administered by maintenance therapy, such as, e.g., once a week, once a month, once every two months, once every three months or once every six months, for a period of 6, 7, 8, 9, 10, 11, 12 months or more.

For example, the agonistic antibodies or antigen-binding fragments thereof that specifically bind CD40 of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Pharmaceutical compositions containing a small molecule CSF-1R inhibitor as the active ingredient can be prepared by intimately mixing the compound with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical composition, a small molecule CSF-1R inhibitor, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. In certain embodiments, the pharmaceutical compositions herein will contain, per unit dosage unit, e.g., tablet, capsule, powder, injection, suppository, teaspoonful and the like, of from about 0.1 mg to about 2000 mg (preferably about 1 mg to about 1000 mg, more preferably, about 1 mg to about 500 mg, more preferably about 10 mg to about 300 mg, for example about 1 mg, about 5 mg, 10 mg, about 25 mg, about 50 mg, about 100 mg, about 150 mg, about 200 mg, about 300 mg, about 500 mg about 600 mg or about 1000 mg), or any amount or range therein, and may be given at a dosage of from about 0.1 mg/kg/day to about 50.0 mg/kg/day, preferably from about 0.5 mg/kg/day to about 25 mg/kg/day, more preferably from about 0.75 mg/kg/day to about 15 mg/kg/day, more preferably from about 2 mg/kg/day to about 10 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from 0.1 to about 2000 mg, or any amount or range therein, of the active ingredient of the present invention. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

To prepare certain pharmaceutical compositions of the present invention, a small molecule CSF-1R inhibitor, as the active ingredient as the active ingredient may be intimately admixed with a pharmaceutical carrier according to conventional pharmaceutical compounding techniques, which carrier may take a wide variety of forms depending of the form of preparation desired for administration (e.g. oral or parenteral) and thereafter be separately combined together. To prepare further pharmaceutical compositions, a small molecule CSF-1R inhibitor, as the active ingredient, may be intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain, the disclosure of which is hereby incorporated by reference.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc., the disclosures of which are hereby incorporated by reference.

The daily dosage of the small molecule CSF-1R inhibitor may be varied over a wide range from 0.1 to 50 mg/kg, or any amount or range therein, per adult human per dosing period. For oral administration, the small molecule CSF-1R inhibitor may be preferably provided in the form of tablets containing about 0.1, 0.5, 1, 2, 2.5, 4, 5, 7.5, 6, 10, 12, 15, 16, 20, 25, 30, 35, 40, 45, 50, 60, 70, 75, 80, 90, 100, 125, 150, 175, 200, 250, 300, 400, 500, 600, 700, 750, 800, 900, 1000, 1200, 1250, 1500, 1750 or 2000 milligrams of the active ingredient(s) for the symptomatic adjustment of the dosage to the patient to be treated. An effective amount of the active ingredient(s) is ordinarily supplied at a dosage level of from about 0.1 mg/kg/day to about 50.0 mg/kg/day, preferably from about 0.5 mg/kg/day to about 25 mg/kg/day, more preferably from about 0.75 mg/kg/day to about 20 mg/kg/day, more preferably from about 2 mg/kg/day to about 10 mg/kg/day, or any range therein. The active ingredient(s) may be administered on a regimen of 1 to 4 times per day, concurrently, sequentially, separately or in a single dosage form.

Optimal dosages to be administered may be readily determined by those skilled in the art, and will vary with the particular compound, co-therapy or combination therapy used, the mode(s) of administration, the strength(s) of the preparation(s), and the advancement of the disease or condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

Example 1: MC38 Tumor Size Assay

Female C57BL/6 mice (Charles River) were eight weeks old on Day 1 of the study and had a BW range of 18.1 to 23.8 g. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ bedding in static microisolators on a 12-hour light cycle at 20-22° C. (68-72° F.) and 40-60% humidity.
Tumor Cell Culture MC38 murine colon carcinoma cells were grown in Dulbecco's Modified Eagle Medium (DMEM) supplemented with 10% fetal bovine serum and 2 mM glutamine, 100 units/mL penicillin G sodium, 100 µg/mL streptomycin sulfate, and 25 µg/mL gentamicin. Cell cultures were maintained in tissue culture flasks in a humidified incubator at 37° C., in an atmosphere of 5% CO2 and 95% air.
Tumor Implantation and Measurement The MC38 colon cells used for implantation were harvested during log phase growth and re-suspended in cold PBS. Mice were anesthetized with isoflurane prior to implantation. Each mouse was injected subcutaneously in the right flank with $1\times10^6$ tumor cells (0.1 mL cell suspension) and tumors were monitored as their volumes approached the target range of 350 to 500 mm³. Seventeen days after tumor implantation, on Day 1 of the study, animals with individual tumor volumes ranging from 256 to 550 mm³ were sorted into fourteen groups (n=10) with group mean tumor volumes of 363-368 mm³. Tumors were measured with calipers twice weekly in two dimensions. Tumor size was calculated using the formula:

$$\text{Tumor Volume (mm}^3\text{)} = \frac{w^2 \times l}{2}$$

where w=width and l=length, in mm, of a tumor. Tumor weight was estimated with the assumption that 1 mg is equivalent to 1 mm³ of tumor volume.
Test Compounds The compound of formula (I), rat IgG2a (Clone 2A3) (5.55 mg/mL, Lot No. 5679-2-4-5-6/0615 and 9.12 mg/mL, Lot No. PRC—Apr. 29, 2015) and anti-mCD40 (FGK45, 7.24 mg/mL, purchased from BioXCell, anti-mouse CD40, Clone: FGK45, SKU: 13E0016-2, Lot No. 5345/0515) and anti-CSF1R (8.52 mg/mL, purchased from BioXCell anti-mouse CSF1R (CD115), Clone: AFS98, SKU: BE0213, Lot. No. 5868/0915) were used as test compounds, alone and in combination. The compound of formula (I) was stored at room temperature and antibody stock solutions were stored at 4° C. upon receipt.

Each week of dosing, the compound of formula (I) was dissolved in 0.5% HPMC to yield a 1.0 mg/mL dosing solution. The dosing solution was stored at 4° C., protected from light. The rat IgG2a isotype and anti-CSF1R dosing solutions were prepared fresh each day by diluting aliquots of the stock solutions with PBS to yield 1.0 mg/mL dosing solutions. The dosing solutions were stored at 4° C., protected from light. The anti-mCD40 dosing solution was prepared fresh each day by diluting an aliquot of the stock solution with PBS to yield a 0.1 mg/mL dosing solution. The dosing solution was stored at 4° C., protected from light.
Treatment/Procedure On Day 1 of the study, fourteen groups of C57BL/6 mice (n=10) began dosing according to the following protocol.

| Group # | Dosing Compound, Regimen |
|---|---|
| Group 1 | rat IgG2a (2A3) on Days 1, 5 and 9. |
| Group 2 | vehicle, twice daily for fourteen days, with one dose on Day 1 (bid ×14). |
| Group 3 | anti-mCD40 (FGK45) on Days 1, 5 and 9. |
| Group 4 | Compound of formula (I), bid × 14. |
| Group 5 | anti-CSF1R on Days 1, 5 and 9. |
| Group 6 | Compound of formula (I), bid × 14, and anti-mCD40 (FGK45) on Days 1, 5 and 9. |
| Group 7 | anti-mCD40 (FGK45) and anti-CSF1R Both administered on Days 1, 5 and 9 |
| Group 8 | Compound of formula (I), bid × 14, and anti-mCD40 (FGK45) on Days 4, 8 and 12. |
| Group 9 | anti-mCD40 (FGK45) on Days 1, 5 and 9 and Compound of formula (I), bid × 14, beginning on Day 4. |
| Group 10 | anti-CSF1R on Days 1, 5 and 9 anti-mCD40 (FGK45) on Days 4, 8 and 12 |
| Group 11 | anti-mCD40 (FGK45) on Days 1, 5 and 9 anti-CSF1R on Days 4, 8 and 12 |
| Group 12 | anti-mCD40 (FGK45) on Days 4, 8 and 12. |
| Group 13 | anti-CSF1R on Days 4, 8 and 12 |
| Group 14 | Compound of formula (I), bid × 14, beginning on Day 4. |

The vehicle (0.5% HPMC) and the compound of formula (I) were administered orally (p.o.). The rat IgG2a isotype control, anti-mCD40, and anti-CSF1R were administered intraperitoneally (i.p.). Rat IgG2a(2A3) was administered at 5 mg/kg. The compound of formula (I) and anti-CSF1R were administered at 10 mg/kg, and anti-mCD40 was administered at 1 mg/kg. The dosing volume for all animals was 10 mL/kg (0.2 mL per 20-g mouse) and was adjusted for body weight.
Tumor Growth Inhibition (TGI) Analysis Tumors were measured using calipers twice per week. The study endpoint was originally defined as a mean tumor volume of 1500 mm³ in the control group or 18 days, whichever came first. TGI (tumor growth inhibition) analysis was performed on Day 15. The MTV (n), the median tumor volume for the number of animals, n, on Day 15, was determined for each group. Percent tumor growth inhibition (% TGI) was defined as the difference between the MTV of the designated control group (Group 1) and the MTV of the drug-treated group, expressed as a percentage of the MTV of the control group:

$$\% \ TGI = \left( \frac{MTV_{control} - MTV_{drug\text{-}related}}{MTV_{control}} \right) \times 100 = [1 - (MTV_{drug\text{-}related} / MTV_{control})] \times 100$$

The data set for TGI analysis included all animals in a group, except those that died due to treatment-related or non-treatment related causes Tumor Growth Delay Animals were monitored individually for tumor growth until Day 61. The study protocol specified a tumor growth delay assay based on the median time-to-endpoint (TTE) in a treated group versus the control group. Each animal was marked for tumor progression (TP) when its tumor reached the 1500 mm³ volume endpoint. The TTE for each mouse was calculated with the following equation:

$$TTE = \frac{\log_{10} \ (\text{endpoint volume}) - b}{m}$$

where b is the intercept and m is the slope of the line obtained by linear regression of a log-transformed tumor growth data set. The data set comprised the first observation that exceeded the study endpoint volume and the three consecutive observations that immediately preceded the attainment of the endpoint volume. Any animal that did not reach endpoint was euthanized at the end of the study and assigned a TTE (time-to-endpoint) value equal to the last day of the study (Day 61). In instances in which the log-transformed calculated TTE preceded the day prior to reaching endpoint or exceeded the day of reaching tumor volume endpoint, a linear interpolation was performed to approximate TTE.

On Day 61, MTV (n) was defined as the median tumor volume of the number of animals, n, that survived to the last day and whose tumors had not reached the volume endpoint. Any animal determined to have died from treatment-related (TR) causes was assigned a TTE value equal to the day of death. Any animal that died from non-treatment-related (NTR) causes was excluded from the analysis. Treatment outcome was evaluated from tumor growth delay (TGD), which was defined as the increase in the median TTE for a treatment group compared to the control group:

TGD=T-C expressed in days, or as a percentage of the median TTE of the control group:

$$\% \ TGD = \frac{T - C}{C} \times 100$$

where T=median TTE for a treatment group, and C=median TTE for the control group.

Criteria for Regression Responses

Treatment efficacy was also determined from the number of regression responses. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm³ for one or more of these three measurements. In a CR response, the tumor volume was less than 13.5 mm³ for three consecutive measurements during the course of the study. Any animal with a CR response on the last day of the study was additionally classified as a tumor-free-survivor (TFS).

Toxicity

Animals were weighed daily for the first five days of the study and twice weekly thereafter. The mice were observed frequently for health and overt signs of any adverse treatment related TR side effects, and noteworthy clinical observations were recorded. Individual body weight loss was monitored per protocol, and any animal with weight loss exceeding 30% for one measurement, or exceeding 25% for three measurements, was euthanized for health as a TR death. If group mean body weight recovered, dosing was resumed in that group, but at a lower dose or less frequent dosing schedule. Acceptable toxicity was defined as a group mean BW loss of less than 20% during the study and not more than one TR death among ten treated animals, or 10%. Any dosing regimen resulting in greater toxicity was considered above the maximum tolerated dose (MTD). A death was classified as TR if it was attributable to treatment side effects as evidenced by clinical signs and/or necropsy, or was classified as TR if due to unknown causes during the dosing period or within 14 days of the last dose. A death was classified as NTR if there was evidence that the death was related to the tumor model, rather than treatment-related. NTR deaths were categorized as NTRa (due to accident or human error), NTRm (due to necropsy-confirmed tumor dissemination by invasion or metastasis), and NTRu (due to unknown causes).

Statistical Analyses

Prism (GraphPad) for Windows 6.07 was used for graphical presentations and statistical analyses. Two-tailed statistical analyses were conducted at significance level P=0.05. Prism summarizes test results as not significant (ns) at P>0.05, significant (symbolized by "*") at 0.01<P≤0.05, very significant ("") at 0.001<P≤0.01, and extremely significant ("*") at P≤0.001. Because tests of statistical significance do not provide an estimate of the magnitude of the difference between groups, all levels of significance were described as either significant or not significant. Groups with regimens that exceeded the limits for acceptable toxicity were not evaluated statistically.

Statistical analyses of the differences between Day 15 median tumor volumes (MTVs) of two groups were accomplished using the Mann-Whitney U test. Survival was analyzed by the Kaplan-Meier method. The log rank (Mantel-Cox) and Gehan-Breslow-Wilcoxon tests determined the significance of the difference between the overall survival experiences (survival curves) of two groups, based on TTE values. When an animal exited the study because of tumor size, the final tumor volume recorded for the animal was included with the data used to calculate the median volume at subsequent time points.

Efficacy Results

Overall tumor response for the tested groups was as listed in Table 2, below. Median TTE is the median time-to-endpoint as defined in the procedure above. T–C is the difference in time-to-endpoint of the treated group versus the control group. % TGD is percent tumor growth delay, calculated as defined above. MTV represents the median tumor volume for the number of animals on the day of the analysis, where (n) represents the number of animals. Regression was defined as PR (partial), CR (complete) or TFS (tumor free survivors).

TABLE 2

Response Summary by Treatment Group

| Group # | Median TTE | T − C | % TGD | Day 61 MTV (n) | Regression PR | CR | TFS |
|---|---|---|---|---|---|---|---|
| 1 | 15.0 | | | | 0 | 0 | 0 |
| 2 | 16.0 | 1.0 | 7 | | 0 | 0 | 0 |
| 3 | 25.4 | 10.4 | 69 | 1268 (1) | 0 | 0 | 0 |
| 4 | 17.5 | 2.5 | 17 | | 0 | 0 | 0 |
| 5 | 15.8 | 0.8 | 5 | | 0 | 0 | 0 |
| 6 | 45.5 | 30.5 | 203 | 2 (4) | 3 | 1 | 1 |
| 7 | 17.9 | 2.9 | 19 | 0 (1) | 0 | 1 | 1 |
| 8 | 57.0 | 42.0 | 280 | 63 (5) | 5 | 0 | 0 |
| 9 | 29.1 | 14.1 | 94 | 4 (1) | | 1 | 1 |
| 10 | 26.2 | 11.2 | 75 | 4 (3) | 1 | 2 | 2 |
| 11 | 33.5 | 18.5 | 123 | 14 (3) | 4 | 0 | 0 |
| 12 | 17.9 | 2.9 | 19 | | 0 | 0 | 0 |
| 13 | 16.5 | 1.5 | 10 | | 0 | 0 | 0 |
| 14 | 11.4 | −3.6 | −24 | | 0 | 0 | 0 |

Tumor growth inhibition results for the tested groups were as listed in Table 3, below. MTV represents the median tumor volume for the number of animals on the day of the analysis, where (n) represents the number of animals. % TGI represents the percent tumor growth inhibition compared to the control Group 1, calculated as defined in the procedure above. Regression was defined as PR (partial) or CR (complete). BW lists the change in mean body weight for all the animals in the group.

TABLE 3

Tumor Growth Inhibition by Treatment Group

| Group | Day 15 MTV (n) | % TGI | Regression PR | CR | Mean BW Nadir (%) |
|---|---|---|---|---|---|
| 1 | 1743 (10) | | 0 | 0 | |
| 2 | 1460 (10) | 16 | 0 | 0 | −0.6 Day 3 |
| 3 | 757 (10) | 57 | 0 | 0 | −4.1 Day 3 |
| 4 | 1376 (10) | 21 | 0 | 0 | −0.3 Day 3 |
| 5 | 1479 (10) | 15 | 0 | 0 | −1.6 Day 2 |
| 6 | 625 (10) | 64 | 3 | 1 | −3.0 Day 2 |
| 7 | 1183 (9) | 32 | 0 | 1 | −3.4 Day 2 |
| 8 | 900 (10) | 48 | 5 | 0 | −1.9 Day 5 |
| 9 | 795 (10) | 54 | 0 | 1 | 4.1 Day 2 |
| 10 | 818 (10) | 53 | 1 | 2 | −4.6 Day 5 |
| 11 | 288 (10) | 83 | 4 | 0 | −5.7 Day 2 |
| 12 | 1411 (10) | 19 | 0 | 0 | −4.0 Day 5 |
| 13 | 1268 (9) | 27 | 0 | 0 | −0.1 Day 5 |
| 14 | 2165 (10) | −24 | 0 | 0 | −0.5 Day 12 |

Tumor Growth in Control Mice (Group 1)

Group 1 mice received rat IgG2a(2A3) isotype control at 5 mg/kg, i.p., and served as controls for all TGI and TGD calculations and for statistical comparisons. The Day 15 MTV (10) was 1743 mm$^3$, with a range of 288 to 3035 mm$^3$. The median TTE of 15.0 days established a maximum possible T−C of 46.0 days (307%) in the 61-day study. All ten control tumors progressed to the 1500 mm$^3$ volume with a range of TTEs from 9.3 to 45 days. Median tumor growth for Group 1 controls was progressive.

Tumor Growth in Vehicle-Treated Mice (Group 2)

Group 2 received vehicle, p.o., bid×14. The Day 15 MTV(10) was 1460 mm$^3$, or a non-significant 16% TGI. All ten animals reached tumor endpoint and the median TTE was 16.0 days, or a non-significant 7% TGD. The median tumor growth for Group 2 animals was very similar to that of Group 1 animals.

Response to Anti-mCD40 (FGK45) Monotherapy (Groups 3 and 12)

Group 3 received anti-mCD40 (FGK45) at 1 mg/kg, administered i.p. on Days 1, 5 and 9. The Day 15 MTV(10) was 757 mm$^3$, or a non-significant 57% TGI. The median TTE was 25.4 days corresponding to a non-significant 69% TGD. There was one survivor with a Day 61 tumor volume of 1268 mm$^3$.

Group 12 received anti-mCD40 (FGK45) at 1 mg/kg, administered i.p. on Days 4, 8 and 12. The Day 15 MTV(10) was 1411 mm$^3$, or a non-significant 19% TGI. The median TTE was 17.9 days corresponding to a non-significant 19% TGD.

Response to Compound of Formula (I) Monotherapy (Groups 4 and 14)

Group 4 received the compound of formula (I) at 10 mg/kg, administered p.o. bid×14. The Day 15 MTV(10) was 1376 mm$^3$, or a non-significant 21% TGI. The median TTE was 17.5 days corresponding to a non-significant 17% TGD.

Group 14 received the compound of formula (I) at 10 mg/kg, administered p.o. bid×14 beginning on Day 4. The Day 15 MTV(10) was 2165 mm$^3$, or a non-significant −24% TGI. The median TTE was 11.4 days corresponding to a non-significant −24% TGD.

Response to Anti-CSF1R Monotherapy (Groups 5 and 13)

Group 5 received anti-CSF1R at 10 mg/kg, administered i.p on Days 1, 5 and 9. The Day 15 MTV(10) was 1479 mm$^3$, or a non-significant 15% TGI. The median TTE was 15.8 days, corresponding to a non-significant 5% TGD.

Group 13 received anti-CSF1R at 10 mg/kg, administered i.p on Days 4, 8 and 12. The Day 15 MTV(9) was 1268 mm$^3$, or a non-significant 27% TGI. One animal had already been removed from the study for TP. The median TTE was 16.5 days, corresponding to a non-significant 10% TGD.

Response to Compound of Formula (I) and Anti-mCD40 (FGK45) Combination Therapy (Groups 6, 8, and 9)

Group 6 received the compound of formula (I) at 10 mg/kg, administered p.o. bid×14 and anti-mCD40 (FGK45) at 1 mg/kg, administered i.p. on Days 1, 5 and 9. The Day 15 MTV(10) was 625 mm$^3$, or a significant 64% TGI (P<0.01, Mann-Whitney). Results were significant when compared to Group 4-compound of formula (I) treated animals (P<0.05, Mann-Whitney) but not Group 3 anti-mCD40 (FGK45)-treated animals. The median TTE was 45.5 days corresponding to 203% TGD. There were four survivors with an MTV (4) on Day 61 of 2 mm$^3$. There were three PRs and one CR in an animal which ended the study as TFS (tumor free survivor). The survival extension for Group 6 was significant when compared to Group 1 control animals (P<0.001, log rank), Group 4 compound of formula (I) treated animals (P<0.01, log rank), and Group 3 anti-mCD40 (FGK45)-treated animals (P<0.05, log rank).

Group 8 received compound of formula (I) at 10 mg/kg, administered p.o. bid×14 and anti-mCD40 (FGK45) at 1 mg/kg, administered i.p. on Days 4, 8 and 12. The Day 15 MTV (10) was 900 mm$^3$, or a significant 48% TGI (P<0.01, Mann-Whitney). Results were also significant when compared to Group 4 compound of formula (I) treated animals (P<0.05, Mann-Whitney) but not Group 12 anti-mCD40 (FGK45)-treated animals. The median TTE was 57.0 days corresponding to 280% TGD. There were five survivors with an Day 61 MTV(5) of 63 mm$^3$ and five PRs. The survival extension for Group 8 was significant when compared to Group 1 control animals, Group 4 compound of formula (I) treated animals, and Group 12 anti-mCD40 (FGK45)-treated animals (P<0.001 for all comparisons, log rank).

Group 9 received anti-mCD40 (FGK45) at 1 mg/kg, administered i.p. on Days 1, 5 and 9 and compound of formula (I) at 10 mg/kg, administered p.o. bid×14 beginning on Day 4. The Day 15 MTV(10) was 795 mm$^3$, or a non-significant 54% TGI. Results were significant when compared to Group 14 compound of formula (I) treated animals (P<0.05, Mann-Whitney) but not Group 3 anti-mCD40 (FGK45)-treated animals. The median TTE was 29.1 days corresponding to 94% TGD. There was one TFS with a Day 61 tumor volume of 4 mm$^3$. The survival extension for Group 9 was not significant when compared to Group 1 control animals, Group 14 compound of formula (I) treated animals, or Group 3 antimCD40 (FGK45)-treated animals.

Response to Anti-mCD40 (FGK45) and Anti-CSF1R Combination Therapy (Groups 7, 10 and 11)

Group 7 received anti-mCD40 (FGK45) at 1 mg/kg and anti-CSF1R at 10 mg/kg, both administered i.p. on Days 1, 5 and 9. The Day 15 MTV(9) was 1183 mm$^3$, or a nonsignificant 32% TGI. One animal was euthanized for health reasons on Day 8 for nTRu (non-treatment related death due to unknown etiology). Results were not significant when compared to Group 3 anti-mCD40 (FGK45)-treated animals or Group 5 anti-CSF1R-treated animals. The median TTE was 17.9 days corresponding to 19% TGD. There was one Day 61 survivor with negligible tumor volume (CR/TFS). The survival extension for Group 7 was not significant when compared to Group 1 control animals, Group 5 anti-CSF1R-treated animals, or Group 3 anti-mCD40 (FGK45)-treated animals.

Group 10 received anti-CSF1R at 10 mg/kg, i.p., on Days 1, 5 and 9 and anti-mCD40 (FGK45) at 1 mg/kg, i.p., on Days 4, 8 and 12. The Day 15 MTV(10) was 818 mm$^3$, or a significant 53% TGI (P<0.05, Mann-Whitney, Table 3). Results were also significant when compared to Group 5 anti-CSF1R-treated animals (P<0.01, Mann-Whitney) but not Group 12 animals, treated with anti-mCD40 (FGK45) on Days 4, 8 and 12. The median TTE was 26.2 days corresponding to 75% TGD. There were three survivors with an MTV(3) on Day 61 of 4 mm$^3$. There was one PR and two CRs/TFS. The survival extension for Group 10 was significant when compared to Group 1 control animals (P<0.01, log rank) and Group 5 anti-CSF1R-treated animals (P<0.05, log rank), but not Group 12 animals.

Group 11 received anti-mCD40 (FGK45) at 1 mg/kg, i.p., on Days 1, 5 and 9 and anti-CSF1R at 10 mg/kg i.p., on Days 4, 8 and 12. The Day 15 MTV(10) was 288 mm$^3$, or a significant 83% TGI (P<0.05, Mann-Whitney, Table 3). Results were not significant when compared to Group 13 anti-CSF1R-treated animals or Group 3 anti-mCD40 (FGK45)-treated animals. The median TTE was 33.5 days corresponding to 123% TGD. There were three survivors with an MTV(3) on DAY 61 of 14 mm$^3$ and four PRs. The survival extension for Group 11 was significant when compared to Group 1 control animals and Group 13 anti-CSF1R-treated animals (P<0.05 for both comparisons, log rank) but not to Group 3 anti-mCD40 (FGK45) treated animals.

Summary

Treatment with three doses of anti-mCD40 (FGK45) produced non-significant results whether administered beginning on Day 1 (57% TGI, P>0.05) or Day 4 (19% TGI,P>0.05). There was a delay in tumor growth afforded to animals when treatment with anti-mCD40 (FGK45) began on Day 1 (69% TGD) but not Day 4 (19% TGD); results were not significant on either dosing regimen (P>0.05 for both comparisons). There was no significant TGI exhibited by animals treated with the compound of formula (I) whether administered twice daily beginning on Day 1 (21% TGI, P>0.05) or Day 4 (−24% TGI, P>0.05). No significant survival advantage was afforded to animals treated with the compound of formula (I) monotherapy (17% TGD for Day 1 and −24% TGD for Day 4 dosing, P>0.05 for both comparisons).

Combination groups of the compound of formula (I) and anti-mCD40 (FGK45) were evaluated in which antibodies were both given on Day 1 (Group 6), the compound of formula (I) on Day 1 and anti-mCD40 (FGK45) on Day 4 (Group 8), or anti-mCD40 (FGK45) on Day 1 and the compound of formula (I) on Day 4 (Group 9). The resultant TGIs of 64% (Group 6) and 48% (Group 8) were significant compared to the control group (P<0.01 for both comparisons), while that of Group 9 (54% TGI) was not. In all cases results were significant when compared to the equivalent compound of formula (I) monotherapy (P<0.05 for all comparisons) but not significant when compared to the equivalent anti-mCD40 (FGK45) monotherapy. The treatments with these combination therapies that resulted in significant survival extensions were Group 6 (203% TGD, four survivors, three PRs, one CR/TFS) and Group 8 (280% TGD, five survivors, five PRs; P<0.001 for both comparisons). Group 9 results (94% TGD, one TFS) were not significant. Groups 6 and 8 results were also significant when compared to the equivalent compound of formula (I) monotherapy (P<0.01 for Group 6 and P<0.001 for Group 8) and the equivalent anti-mCD40 (FGK45) monotherapy (P<0.05 for Group 6 and P<0.001 for Group 8).

Thus, combination treatments with the compound of formula (I)/anti-mCD40 (FGK45) resulted in significant TGIs and survival extensions unless treatment with the compound of formula (I) began on Day 4.

Combination groups of anti-CSF1R and anti-mCD40 (FGK45) were evaluated in which antibodies were both given on Day 1 (Group 7), anti-CSF1R on Day 1 and anti-mCD40 (FGK45) on Day 4 (Group 10), or anti-mCD40 (FGK45) on Day 1 and anti-CSF1R on Day 4 (Group 11). Combination therapies were most efficacious when one of the treatments was started on Day 4. The resultant TGIs of 53% (Group 10), and 83% (Group 11) were significant compared to the control group (P<0.05) while that of Group 7 (32%) was not. Only for Group 10 were results significant when compared to the equivalent anti-CSF1R monotherapy (P<0.01). The only combination therapies that resulted in significant survival extensions were Group 10 (75% TGD, three survivors, one PR, two CR/TFS, P<0.01) and Group 11 (123% TGD, three survivors, four PRs; P<0.05). Group 7 results (19% TGD, one TFS) were not significant. For Groups 10 and 11 results were also significant when compared to the equivalent anti-CSF1R monotherapy (P<0.05 for both comparisons) but not the equivalent anti-mCD40 (FGK45) monotherapy.

Thus, combination treatments with anti-mCD40 (FGK45) and anti-CSF1R resulted in significant TGIs and survival extensions when compared to control animals, as long as one test article was administered beginning on Day 4.

Example 2: CT26 Tumor Size Assay

Methods and Materials

Female BALB/c mice (BALB/c AnNcr1, Charles River) were eight weeks old on Day 1 of the study and had a BW range of 15.5 to 19.9 g. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ bedding in static microisolators on a 12-hour light cycle at 20-22° C. (68-72° F.) and 40-60% humidity.

Tumor Cell Culture

CT26 murine colon carcinoma cells were grown in RPMI-1640 medium containing 10% fetal bovine serum, 2 mM glutamine, 100 units/mL penicillin G sodium, 100 μg/mL streptomycin sulfate, and 25 μg/mL gentamicin. The cells were cultured in tissue culture flasks in a humidified incubator at 37° C., in an atmosphere of 5% CO2 and 95% air.

Tumor Implantation and Measurement

The CT26 colon cells used for implantation were harvested during log phase growth and re-suspended in cold PBS. Each mouse was injected subcutaneously in the right flank with 3×105 tumor cells (0.1 mL cell suspension) and tumors were monitored as their volumes approached the target range of 75 to 125 mm3. Fourteen days after tumor implantation, on Day 1 of the study, animals with individual tumor volumes ranging from 75 to 125 mm$^3$ were sorted into fourteen groups (n=10) with group mean tumor volumes of 118-119 mm3. Tumors were measured with calipers twice weekly in two dimensions.

Tumor size was calculated using the formula:

$$\text{Tumor Volume (mm}^3\text{)} = \frac{w^2 \times l}{2}$$

where w=width and l=length, in mm, of a tumor. Tumor weight was estimated with the assumption that 1 mg is equivalent to 1 mm3 of tumor volume.

Test Compounds

The compound of formula (I), rat IgG2a (Clone 2A3) (5.55 mg/mL), anti-mCD40 (Clone FGK45) (5.46 mg/mL, purchased from BioXCell, anti-mouse CD40, Clone: FGK45, SKU: 13E0016-2, Lot No. 4699/0614B), and anti-CSF1R (5.41 mg/mL, purchased from BioXCell anti-mouse CSF1R (CD115), Clone: AFS98, SKU: BE0213, Lot No. 5248/0814) were used as test compounds, alone and in combination. The compound of formula (I) was stored at room temperature and antibody stock solutions were stored at 4° C. upon receipt.

Each week of dosing, the compound of formula (I) was dissolved in 0.5% HPMC to yield a 1.0 mg/mL dosing solution. The dosing solution was stored at 4° C., protected from light. The rat IgG2a isotype and anti-CSF1R dosing solutions were prepared fresh each day by diluting aliquots of the stock solutions with PBS to yield 1.0 mg/mL dosing solutions. The dosing solutions were stored at 4° C., protected from light. The anti-mCD40 dosing solution was prepared fresh each day by diluting an aliquot of the stock solution with PBS to yield a 0.5 mg/mL dosing solution. The dosing solution was stored at 4° C., protected from light.

Treatment/Procedure

On Day 1 of the study, fourteen groups of BALB/c mice (n=10) began dosing according to the following protocol.

| Group # | Dosing Compound, Regimen |
|---|---|
| Group 1 | rat IgG2a (2A3) on Days 1, 5 and 9. |
| Group 2 | vehicle, twice daily for fourteen days, with one dose on Day 1 (bid ×14). |
| Group 3 | anti-mCD40 (FGK45) on Days 1, 5 and 9. |
| Group 4 | compound of formula (I), bid × 14. |
| Group 5 | anti-CSF1R on Days 1, 5 and 9 |
| Group 6 | compound of formula (I), bid × 14, and anti-mCD40 (FGK45) on Days 1, 5 and 9. |
| Group 7 | anti-mCD40 (FGK45) and anti-CSF1R both administered on Day 1, 5 and 9 |
| Group 8 | compound of formula (I), bid × 14, and anti-mCD40 (FGK45) on Days 4, 8 and 12. |
| Group 9 | anti-mCD40 (FGK45) on Days 1, 5 and 9 and compound of formula (I), bid × 14, beginning on Day 4. |
| Group 10 | anti-CSF1R on Days 1, 5 and 9 anti-mCD40 (FGK45) on Days 4, 8 and 12 |
| Group 11 | anti-mCD40 (FGK45) on Days 1, 5 and 9 anti-CSF1R on Days 4, 8 and 12 |
| Group 12 | anti-mCD40 (FGK45) on Days 4, 8 and 12. |
| Group 13 | anti-CSF1R on Days 4, 8 and 12 |
| Group 14 | compound of formula (I), bid × 14, beginning on Day 4. |

The vehicle (0.5% HPMC) and the compound of formula (I) were administered orally (p.o.). The rat IgG2a isotype control, anti-mCD40, and anti-CSF1R were administered intraperitoneally (i.p.). Rat IgG2a(2A3), the compound of formula (I) and the anti-CSF1R were administered at 10 mg/kg. The anti-mCD40 was administered at 5 mg/kg. The dosing volume for all animals was 10 mL/kg (0.2 mL per 20-g mouse) and was adjusted for body weight.

Tumor Growth Inhibition (TGI) Analysis

Tumors were measured using calipers twice per week. The study endpoint was originally defined as a mean tumor volume of 1500 mm$^3$ in the control group or 60 days, whichever came first. Day 15 was chosen for TGI analysis. The MTV (n), the median tumor volume for the number of animals, n, on Day 15, was determined for each group. Percent tumor growth inhibition (% TGI) was defined as the difference between the MTV of the designated control group (Group 1) and the MTV of the drug-treated group, expressed as a percentage of the MTV of the control group:

$$\% \ TGI = \left(\frac{MTV_{control} - MTV_{drug-related}}{MTV_{control}}\right) \times 100 = [1 - (MTV_{drug-related}/MTV_{control})] \times 100$$

The data set for TGI analysis includes all animals in a group, except those that die due to treatment-related (TR) or non-treatment-related (NTR) causes.

Tumor Growth Delay

Animals were monitored individually for tumor growth until Day 39. The study protocol specified a tumor growth delay assay based on the median time-to-endpoint (TTE) in a treated group versus the control group. Each animal was marked for tumor progression (TP) when its tumor reached the 1500 mm$^3$ volume endpoint. The TTE for each mouse was calculated with the following equation:

$$TTE = \frac{\log_{10}(\text{endpoint volume}) - b}{m}$$

where b is the intercept and m is the slope of the line obtained by linear regression of a log-transformed tumor growth data set. The data set comprised of the first observation that exceeded the study endpoint volume and the three consecutive observations that immediately preceded the attainment of the endpoint volume. Any animal that did not reach endpoint was euthanized at the end of the study and assigned a TTE value equal to the last day of the study (Day 39). In instances in which the log-transformed calculated TTE preceded the day prior to reaching endpoint or exceeded the day of reaching tumor volume endpoint, a linear interpolation was performed to approximate TTE. On Day 39, MTV (n) was defined as the median tumor volume of the number of animals, n, that survived to the last day and whose tumors had not reached the volume endpoint. Any animal determined to have died from treatment-related (TR) causes was to be assigned a TTE value equal to the day of death. Any animal that died from non-treatment-related (NTR) causes was to be excluded from the analysis. Treatment outcome was evaluated from tumor growth delay (TGD), which was defined as the increase in the median TTE for a treatment group compared to the control group:

$$TGD = T - C$$

expressed in days, or as a percentage of the median TTE of the control group:

$$\% \, TGD = \frac{T-C}{C} \times 100$$

where T=median TTE for a treatment group, and C=median TTE for the control group.

Criteria for Regression Responses

Treatment efficacy was also determined from the number of regression responses. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm3 for three consecutive measurements during the course of the study. Any animal with a CR response on the last day of the study is additionally classified as a tumor-free-survivor (TFS).

Toxicity

Animals were weighed daily for the first five days of the study and twice weekly thereafter. The mice were observed frequently for health and overt signs of any adverse treatment related (TR) side effects, and noteworthy clinical observations were recorded. Individual body weight loss was monitored per protocol, and any animal with weight loss exceeding 30% for one measurement, or exceeding 25% for three measurements, was to be euthanized for health as a TR death. If group mean body weight recovered, dosing was resumed in that group, but at a lower dose or less frequent dosing schedule. Acceptable toxicity was defined as a group mean BW loss of less than 20% during the study and not more than one TR death among ten treated animals, or 10%. Any dosing regimen resulting in greater toxicity was considered above the maximum tolerated dose (MTD). A death was classified as TR if it was attributable to treatment side effects as evidenced by clinical signs and/or necropsy, or was classified as TR if due to unknown causes during the dosing period or within 14 days of the last dose. A death was classified as NTR if there was evidence that the death was related to the tumor model, rather than treatment-related. NTR deaths were further categorized as NTRa (due to accident or human error), NTRm (due to necropsy-confirmed tumor dissemination by invasion or metastasis), and NTRu (due to unknown causes).

Statistical and Graphical Analyses

Prism (GraphPad) for Windows 6.07 was used for graphical presentations and statistical analyses. Survival was analyzed by the Kaplan-Meier method. The log rank (Mantel-Cox) and Gehan-Breslow-Wilcoxon tests determined the significance of the difference between the overall survival experiences (survival curves) of two groups, based on TTE values. Statistical analyses of the differences between Day 15 median tumor volumes (MTVs) of two groups were accomplished using the Mann-Whitney U test. Comparisons of more than two groups were conducted using the Kruskal-Wallis Dunn test. Two-tailed statistical analyses were conducted at significance level P=0.05. The analyses were not corrected for multiple comparisons. Prism summarizes test results as not significant (ns) at P>0.05, significant (symbolized by "*") at $0.01 < P \leq 0.05$, very significant ("") at $0.001 < P \leq 0.01$, and extremely significant ("*") at $P \leq 0.001$. Because tests of statistical significance do not provide an estimate of the magnitude of the difference between groups, all levels of significance were described as either significant or not. Groups with regimens that exceeded the limits for acceptable toxicity were not evaluated statistically.

Results

Overall tumor response for the tested groups was as listed in Table 4, below. Median TTE is the median time-to-endpoint as defined in the procedure above. T–C is the difference in time-to-endpoint of the treated group versus the control group. % TGD is percent tumor growth delay, calculated as defined above. No animals showed regression.

TABLE 4

Response Summary by Treatment Group

| Group | Median TTE | T-C | % TGD |
| --- | --- | --- | --- |
| 1 | 12.1 | | |
| 2 | 12.9 | 0.8 | 7 |
| 3 | 17.0 | 4.9 | 40 |
| 4 | 13.0 | 0.9 | 7 |
| 5 | 11.9 | -0.2 | -2 |
| 6 | 20.2 | 8.1 | 67 |
| 7 | 17.8 | 5.7 | 47 |
| 8 | 18.3 | 6.2 | 51 |
| 9 | 17.8 | 5.7 | 47 |
| 10 | 16.2 | 4.1 | 34 |
| 11 | 17.0 | 4.9 | 40 |
| 12 | 14.2 | 2.1 | 17 |
| 13 | 12.3 | 0.2 | 2 |
| 14 | 13.9 | 1.8 | 15 |

Tumor growth inhibition results for the tested groups were as listed in Table 5, below. MTV represents the median tumor volume for the number of animals on the day of the analysis, where (n) represents the number of animals. % TGI represents the percent tumor growth inhibition compared to the control Group 1, calculated as defined in the procedure above. No animals showed regression. BW Nadir lists the change in mean body weight for all the animals in the group.

TABLE 5

Tumor Growth Inhibition by Treatment Group

| Group | MTV (n) Day 15 | % TGI | Mean BW Nadir (%) |
|---|---|---|---|
| 1 | 2496 (8) | | |
| 2 | 1775 (8) | 29 | |
| 3 | 1188 (10) | 52 | |
| 4 | 1913 (80) | 23 | |
| 5 | 2667 (8) | −7 | |
| 6 | 725 (10) | 71 | −3.1 Day 4 |
| 7 | 958 (10) | 62 | −1.8 Day 3 |
| 8 | 874 (10) | 65 | |
| 9 | 799 (10) | 68 | |
| 10 | 1334 (10) | 47 | |
| 11 | 1152 (10) | 54 | |
| 12 | 1690 (9) | 32 | |
| 13 | 2213 (6) | 11 | |
| 14 | 1545 (8) | 38 | |

Tumor Growth in Control Mice (Group 1)

Group 1 mice received rat IgG2a(2A3) isotype control at 10 mg/kg, i.p., and served as controls for all TGI (tumor growth inhibition) and TGD (tumor growth delay) calculations and for statistical comparisons. The Day 15 MTV(10) was 2496 mm$^3$. The median TTE of 12.1 days established a maximum possible T–C of 26.9 days (222%) in the 39-day study. All ten control tumors progressed to the 1500 mm$^3$ volume with a range of TTEs from 9.5 to 15.7 days. Median tumor growth for Group 1 controls was progressive.

Tumor Growth in Vehicle-Treated Mice (Group 2)

Group 2 received vehicle, p.o., bid×14. The Day 15 MTV(10) was 1775 mm3, or a non-significant 29% TGI. All ten animals reached tumor endpoint prior with a median TTE of 12.9 days, or a non-significant 7% TGD. The median tumor growth for Group 2 animals was very similar to that of Group 1 animals.

Response to Anti-mCD40 (FGK45) Monotherapy (Groups 3 and 12)

Group 3 received anti-mCD40 (FGK45) at 5 mg/kg, administered i.p. on Days 1, 5 and 9. The Day 15 MTV(10) was 1188 mm$^3$, or a significant 52% TGI (P<0.01, Mann-Whitney, Table 3). The median TTE was 17.0 days corresponding to a significant 40% TGD (P<0.001, log rank).

Group 12 received anti-mCD40 (FGK45) at 5 mg/kg, administered i.p. on Days 4, 8, and 12. The Day 15 MTV(10) was 1690 mm3, or a non-significant 32% TGI (P>0.05, Mann-Whitney, Table 3). The median TTE was 14.2 days corresponding to a significant 17% TGD (P<0.05, log rank).

Response to Compound of Formula (I) Monotherapy (Groups 4 and 14)

Group 4 received the compound of formula (I) at 10 mg/kg, administered p.o. bid×14. The Day 15 MTV(10) was 1913 mm$^3$, or a non-significant 23% TGI. The median TTE was 13.0 days corresponding to a non-significant 7% TGD.

Group 14 received the compound of formula (I) at 10 mg/kg, administered p.o. bid×14 beginning on Day 4. The Day 15 MTV(10) was 1545 mm$^3$, or a non-significant 38% TGI. The median TTE was 13.9 days corresponding to a non-significant 15% TGD.

Response to Anti-CSF1R Monotherapy (Groups 5 and 13)

Group 5 received anti-CSF1R at 10 mg/kg, administered i.p. on Days 1, 5 and 9. The Day 15 MTV(10) was 2667 mm$^3$, or a non-significant −7% TGI when compared to Group 1 control animals (P<0.05, Mann-Whitney). The median TTE was 11.9 days corresponding to a non-significant −2% TGD.

Group 13 received anti-CSF1R at 10 mg/kg, administered i.p. on Days 4, 8, and 12. The Day 15 MTV(10) was 2213 mm$^3$, or a non-significant 11% TGI. The median TTE was 12.3 days, corresponding to a non-significant 2% TGD.

Response to Compound of Formula (I) and Anti-mCD40 (FGK45) Combination Therapy (Groups 6, 8, and 9)

Group 6 received the compound of formula (I) at 10 mg/kg, administered p.o. bid×14 and anti-mCD40 (FGK45) at 5 mg/kg, administered i.p. on Days 1, 5 and 9. The Day 15 MTV(10) was 725 mm$^3$, or a significant 71% TGI (P<0.001, Mann-Whitney). Day 15 results were not significant when compared to Group 3 anti-mCD40 (FGK45)-treated animals (P>0.05, Mann-Whitney), but was significantly improved when compared to Group 4 compound of formula (I) treated animals (P<0.01, Mann-Whitney). The median TTE was 20.2 days corresponding to 67% TGD. The survival extension for Group 6 was significant when compared to Group 1 control animals and Group 4 compound of formula (I) treated animals (P<0.001 for both comparisons, log rank) but not to Group 3 anti-mCD40 (FGK45) treated animals.

Group 8 received the compound of formula (I) at 10 mg/kg, administered p.o. bid×14 and anti-mCD40 (FGK45) at 5 mg/kg, administered i.p. on Days 4, 8 and 12. The Day 15 MTV(10) was 874 mm$^3$, or a significant 65% TGI (P<0.01, Mann-Whitney). Day 15 results were also significant when compared to Group 4 compound of formula (I) treated animals (P<0.001, Mann-Whitney) but not Group 12 anti-mCD40 (FGK45)-treated animals (P>0.05, Mann-Whitney). The median TTE was 18.3 days corresponding to 51% TGD. The survival extension for Group 8 was significant when compared to Group 1 control animals, Group 4 compound of formula (I) treated animals and Group 12 anti-mCD40 (FGK45)-treated animals (P<0.01, log rank).

Group 9 received anti-mCD40 (FGK45) at 5 mg/kg, administered i.p. on Days 1, 5, and 9 and the compound of formula (I) at 10 mg/kg, administered p.o. bid×14 beginning on Day 4. The Day 15 MTV(10) was 799 mm$^3$, or a significant 68% TGI (P<0.01, Mann-Whitney). Results were also significant when compared to Group 14 compound of formula (I) treated animals (P<0.05, Mann-Whitney) but not Group 3 anti-mCD40 (FGK45)-treated animals (P>0.05, Mann-Whitney). The median TTE was 17.8 days corresponding to 47% TGD. The survival extension for Group 9 was significant when compared to Group 1 control animals and Group 14 compound of formula (I) treated animals (P<0.001 for both comparisons, log rank) but not Group 3 anti-mCD40 (FGK45)-treated animals (P>0.05, log rank).

Response to Anti-mCD40 (FGK45) and Anti-CSF1R Combination Therapy (Groups 7, 10, and 11)

Group 7 received anti-mCD40 (FGK45) at 5 mg/kg and anti-CSF1R at 10 mg/kg, both administered i.p. on Days 1, 5 and 9. The Day 15 MTV(10) was 958 mm$^3$, or a significant 62% TGI P<0.001, Mann-Whitney). Results were also significant when compared to Group 5 anti-CSF1R-treated animals (P<0.001, Mann-Whitney) but not significantly improved when compared to Group 3 anti-mCD40 (FGK45)-treated animals (P>0.05, Mann-Whitney). The median TTE was 17.8 days corresponding to 47% TGD. The survival extension for Group 7 was significant when compared to Group 1 control animals and Group 5 anti-CSF1R-treated animals (P<0.001, log rank) but not to Group 3 anti-mCD40 (FGK45)-treated animals.

Group 10 received anti-CSF1R at 10 mg/kg, i.p., on Days 1, 5 and 9 and anti-mCD40 (FGK45) at 5 mg/kg, i.p., on Days 4, 8 and 12. The Day 15 MTV(10) was 1334 mm$^3$, or a significant 47% TGI (P<0.05, Mann-Whitney). Day 15 results were also significant when compared to Group 5 anti-CSF1R-treated animals (P<0.01, Mann-Whitney), but not Group 12 anti-mCD40 (FGK45)-treated animals. The median TTE was 16.2 days corresponding to 34% TGD. The survival extension for Group 10 was significant when compared to Group 1 control animals (P<0.001, log rank), Group 5 anti-CSF1R-treated animals (P<0.001, log rank) and Group 12 anti-mCD40 (FGK45)-treated animals (P<0.05, log rank).

Group 11 received anti-mCD40 (FGK45) at 5 mg/kg, i.p., on Days 1, 5 and 9 and anti-CSF1R at 10 mg/kg i.p., on Days 4, 8 and 12. The Day 15 MTV(10) was 1152 mm$^3$, or a significant 54% TGI (P<0.01, Mann-Whitney). Results were also significant when compared to Group 13 anti-CSF1R-treated animals (P<0.05, Mann-Whitney) but not Group 3 anti-mCD40 (FGK45)-treated animals. The median TTE was 17.0 days corresponding to 40% TGD. The survival extension for Group 11 was significant when compared to Group 1 control animals and Group 13 anti-CSF1R-treated animals (P<0.001, log rank), but not to Group 3 anti-mCD40 (FGK45)-treated animals.

Side Effects

There were no deaths in the study. Group 6 experienced group mean BW losses of 3.1% (Day 4) and 1.8% (Day 3), respectively. No other groups experienced group mean BW losses.

Summary

Treatment with three doses of anti-mCD40 (FGK45) was effective when administered beginning on Day 1 but not when initiated on Day 4. There was a survival benefit afforded to animals and this was significant when treatment with anti-mCD40 (FGK45) began on Day 1 or Day 4. There was no significant TGI exhibited by animals treated with the compound of formula (I) whether administered twice daily beginning on Day 1 or Day 4. No significant survival advantage was afforded to animals treated with compound of formula (I) monotherapy.

Combination groups of the compound of formula (I) and anti-mCD40 (FGK45) were evaluated when administered at different time points. All treatments were efficacious when compared to the control group or compound of formula (I) monotherapies, but were not significantly better than anti-mCD40 (FGK45) monotherapies.

Combination groups of anti-CSF1R and anti-mCD40 (FGK45) were evaluated in which antibodies were administered at different time points. All treatments were efficacious when compared to the control group. In all cases, results were also significant when compared to the equivalent anti-CSF1R monotherapy, but where not significant compared to the equivalent anti-mCD40 (FGK45) monotherapies. All treatments with these combination therapies resulted in significant survival extensions. In most cases results were also significant when compared to the equivalent anti-CSF1R monotherapy and anti-mCD40 (FGK45) monotherapy initiated on Day 4, but not the equivalent anti-mCD40 (FGK45) monotherapy when treatment began on Day 1.

Anti-mCD40 (FGK45) displayed activity as a monotherapy. Combination treatments with the compound of formula (I)/anti-mCD40 (FGK45) or anti-CSF1R/anti-mCD40 (FGK45) resulted in significant TGIs and survival extensions when compared to control animals, regardless of whether treatments began on Day 1 or Day 4. In most cases these results were not significantly different from those of animals treated with anti-mCD40 (FGK45) monotherapy.

Example 3: Mean Tumor Volume Assay

The assay was run using female BALB/c mice (BALB/c AnNcr1, Charles River). The mice were eight weeks old on Day 1 of the study and had a body weight (BW) range of 15.5 to 19.9 g.

CT26 murine colon carcinoma cells were grown in RPMI-1640 medium containing 10% fetal bovine serum, 2 mM glutamine, 100 units/mL penicillin G sodium, 100 μg/mL streptomycin sulfate, and 25 μg/mL gentamicin. The cells were cultured in tissue culture flasks in a humidified incubator at 37° C., in an atmosphere of 5% CO2 and 95% air.

The CT26 colon cells used for implantation were harvested during log phase growth and re-suspended in cold phosphate buffered saline (PBS).

Each mouse was injected subcutaneously in the right flank with 1×10^6 tumor cells (0.1 mL cell suspension) and tumors were monitored as their volumes approached the target range of 75 to 125 mm$^3$. Day 1 of the study, animals with individual tumor volumes ranging from 75 to 125 mm$^3$ were randomized into six different groups (n=12).

The compound of formula of formula (I), rat IgG2a (Clone 2A3) (5.55 mg/mL), anti-CSF1R (purchased from BioXCell anti-mouse CSF1R (CD115), Clone: AFS98, SKU: BE0213, Lot No. 5248/0814) and anti-mCD40 (purchased from BioXCell, anti-mouse CD40, Clone: FGK45, SKU: 13E0016-2-) were used as test compounds, alone or in combination. The compound of formula (I) was stored at room temperature and antibody stock solutions were stored at 4° C. upon receipt. The compound of formula (I) was dissolved in 0.5% HPMC to yield a 1.0 mg/mL dosing solution. The dosing solution was stored at 4° C., protected from light. The rat IgG2a isotype, anti-CD40 and anti-CSF1R dosing solutions were prepared once at the beginning of study by diluting aliquots of the stock solutions with PBS. The dosing solution was stored at 4° C., protected from light.

Treatment Procedure

On Day 1 of the study, groups of BALB/c mice (n=12/group) began dosing according to the following protocol

| | |
|---|---|
| Group 1 | rat IgG2a (2A3) 5 mpk i.p. on Day 1, 5, 9 and 13 and vehicle, twice daily for fourteen days via oral gavage |
| Group 2 | anti-mCD40 (FGK45) 5 mpk i.p. on Day 1, 5, 9, and 13 |
| Group 3 | anti-CSF1R 10 mpk i.p. on Day 1, 5, 9 and 13 |
| Group 4 | Compound of formula (I) 10 mpk, b.i.d. × 14 days |
| Group 4 | anti-mCD40 (FGK45) 5 mpk and anti-CSF1R 10 mpk, both administered on Days 1, 5, 9 and 13 i.p. |
| Group 6 | Compound of formula (I) 10 mpk b.i.d. × 14 days, and anti-mCD40 (FGK45) 5 mpk on Days 1, 5, 9 and 13 i.p. |

The vehicle (0.5% HPMC) and compound of formula (I) were administered orally (p.o.). The rat IgG2a isotype control, anti-mCD40 and anti-CSF1R were administered intraperitoneally (i.p.). Rat IgG2a(2A3), the anti-CSF1R and compound of formula (I) were administered at 10 mg/kg. The anti-mCD40 was administered at 5 mg/kg. The dosing volume for all animals was 10 mL/kg (0.2 mL per 20-g mouse) and was adjusted for body weight.

Seven days after the start of the treatments, six mice from each group were euthanized and tumors, spleens, lymph nodes and blood were harvested. Tissues were placed into 10% RPMI and kept on ice until further processing. Tumors were processed using MACS Miltenyi Kit per manufacturer's instruction into single-cell suspension. Spleens and lymph nodes were processed into single-cell suspensions via manual mechanical disruption. Cells were further stained and analyzed by flow cytometry analysis. Antibodies were obtained either from BioLegend or BD Biosciences. Flowjo was used to analyze the flow cytometry.

Results

Measured group mean tumor volume (mm$^3$) and calculated % tumor growth inhibition relative to Group 1 (control animals) for each group at select time-points were as shown in Table 6, below.

TABLE 6

| Group | Day 6 | Day 8 | Day 10 | Day 13 | Day 15 | Day 16 | Day 20 |
|---|---|---|---|---|---|---|---|
| Response Summary by Treatment Group | | | | | | | |
| Group Mean Tumor Volume in mm³ | | | | | | | |
| 1 | 106.77 | 121.87 | 157.58 | 264.82 | 414.79 | 403.47 | 884.72 |
| 2 | 100.97 | 13.9.16 | 203.40 | 250.79 | 403.21 | 352.84 | 764.90 |
| 3 | 109.02 | 138.33 | 236.83 | 399.53 | 661.53 | 805.00 | 1018.36 |
| 4 | 107.69 | 130.14 | 196.09 | 268.17 | 392.41 | 412.91 | 739.49 |
| 5 | 101.57 | 147.72 | 215.91 | 303.51 | 433.99 | 371.31 | 583.11 |
| 6 | 103.34 | 127.90 | 153.65 | 157.08 | 151.48 | 186.62 | 326.56 |
| % Tumor Growth Inhibition | | | | | | | |
| 1 | — | — | — | — | — | — | — |
| 2 | 5.44 | −14.19 | −29.07 | 5.30 | 2.79 | 12.55 | 13.54 |
| 3 | −2.10 | −13.51 | −50.29 | −50.87 | −59.49 | −99.52 | −15.11 |
| 4 | −0.86 | −6.79 | −24.44 | −1.27 | 5.39 | −2.37 | 16.42 |
| 5 | 4.87 | −21.21 | −37.01 | −14.61 | −4.63 | 7.97 | 34.09 |
| 6 | 3.22 | −4.95 | 2.50 | 41.82 | 63.48 | 53.75 | 63.09 |

The results presented in Table 6 above show that combination treatments with the compound of formula (I) and anti-mCD40 (FGK45) resulted in greater than additive inhibition of tumor growth on Days 13, 15, 16 and 20. Additionally, combination treatment with the compound of formula (I) and anti-mCD40 (FGK45) exhibited greater inhibition of tumor growth than combination treatment with the anti-CSF1R and anti-mCD40 (FGK45), at each study day measurement.

Although not intended to be definitive or limiting in any way, it is theorized that administration of a small molecule CSF-1R inhibitor prior to or concurrently with the administration of the CD-40 antibody, results in a decrease in the number of tumor associated macrophages, a subset of M2 macrophages (TAMs/M2), which in turn results in improved clinical response. More particularly, it is theorized that administration of a small molecule CSF-1R inhibitor reduces the immunosuppressive TME (which may enhance the efficacy of IO agents), induces a de novo T cell response by removing the suppressive macrophage population; and allows for activity of the IO agent(s) in otherwise non-responsive patients.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

Sequence listing

| SEQ ID NO: | Type | Species | Description | Sequence |
|---|---|---|---|---|
| 1 | PRT | Homo Sapiens | CD40 | MVRLPLQCVLWGCLLTAVHPEPPTACREK QYLINSQCCSLCQPGQKLVSDCTEFTETE CL PCGESEFLDTWNRETHCHQHKYCDPNLGL RVQQKGTSETDTICTCEEGWHCTSEACES CV LHRSCSPGFGVKQIATGVSDTICEPCPVG FFSNVSSAFEKCHPWTSCETKDLVVQQAG TN KTDVVCGPQDRLRALVVIPIIFGILFAIL LVLVFIKKVAKKPTNKAPHPKQEPQEINF PD DLPGSNTAAPVQETLHGCQPVTQEDGKES RISVQERQ |
| 2 | PRT | Artificial sequence | HCDR1 of ADC-1013, A4, A5, C4, G4, F6, F9, H12, B11 | TYGMH |
| 3 | PRT | Artificial sequence | HCDR2 of ADC-1013, A4, A5, G4, F6, F9, H12, B11 | YISGGSSYIFYADSVRG |

| SEQ ID NO: | Type | Species | Description | Sequence |
|---|---|---|---|---|
| 4 | PRT | Artificial sequence | HCDR3 of ADC-1013, A4, A5, C4, G4, F6, F9, H12, B11 | ILRGGSGMDL |
| 5 | PRT | Artificial sequence | LCDR1 of ADC-1013, H12 and B11 | TGSSSNIGAGYNVY |
| 6 | PRT | Artificial sequence | LCDR2 of ADC-1013, A4, C4, G4, F9, H12 and B11 | GNINRPS |
| 7 | PRT | Artificial sequence | LCDR3 of ADC-1013 | AAWDKSISGLV |
| 8 | PRT | Artificial sequence | VH of ADC-1013, A4, A5, G4, F6, F9, H12 and B11 | EVQLLESGGGLVQPGGSLRLSCAASGFTFSTYG MHWVRQAPGKGLEWLSYISGGSSYIFYADSV RGRFTISRDNSENALYLQMNSLRAEDTAVYYC ARILRGGSGMDLWGQGTLVTVSS |
| 9 | PRT | Artificial sequence | VL of ADC-1013 | QSVLTQPPSASGTPGQRVTISCTGSSSNI GAGYNVYWYQQLPGTAPKLLIYGNINRPS GVPDRFSGSKSGTSASLAISGLRSEDEAD YYCAAWDKSISGLVFGGGTKLTVLG |
| 10 | PRT | Artificial sequence | HC of ADC-1013 | EVQLLESGGGLVQPGGSLRLSCAASGFTFSTYG MHWVRQAPGKGLEWLSYISGGSSYIFYADSV RGRFTISRDNSENALYLQMNSLRAEDTAVYYC ARILRGGSGMDLWGQGTLVTVSSASTKGPSV FPLAPSSKSTSGGTAALGCLVKDYFPEPVTVSW NSGALTSGVHTFPAVLQSSGLYSLSSVVTVPSS SLGTQTYICNVNHKPSNTKVDKKVEPKSCDKT HTCPPCPAPELLGGPSVFLFPPKPKDTLMISRT PEVTCVVVDVSHEDPEVKFNWYVDGVEVHN AKTKPREEQYNSTYRVVSVLTVLHQDWLNGK EYKCKVSNKALPAPIEKTISKAKGQPREPQVYT LPPSRDELTKNQVSLTCLVKGFYPSDIAVEWES NGQPENNYKTTPPVLDSDGSFFLYSKLTVDKS RWQQGNVFSCSVMHEALHNHTYQKSLSLSP GK |
| 11 | PRT | Artificial sequence | LC of ADC-1013 | QSVLTQPPSASGTPGQRVTISCTGSSSNI GAGYNVYWYQQLPGTAPKLLIYGNINRPS GVPDRFSGSKSGTSASLAISGLRSEDEAD YYCAAWDKSISGLVFGGGTKLTVLGQPKA APSVTLFPPSSEELQANKATLVCLISDFY PGAVTVAWKADSSPVKAGVETTTPSKQSN NKYAASSYLSLTPEQWKSHRSYSCQVTHE GSTVEKTVAPTECS |
| 12 | PRT | Artificial sequence | HCDR2 of C4 | YISGGSSYIFYADTVRG |
| 13 | PRT | Artificial sequence | LCDR1 fo A4 and C4 | TGSTSNIGAGYKVY |
| 14 | PRT | Artificial sequence | LCDR1 of A5 | TGSSSNIGAGYHVY |
| 15 | PRT | Artificial sequence | LCDR1 of G4 | TGSSSNIGAGYKVY |
| 16 | PRT | Artificial sequence | LCDR1 of F6 | TGSSSNIGAGYDVY |
| 17 | PRT | Artificial sequence | LCDR1 of F9 | TGSSSNIGAGYGVY |

Sequence listing

| SEQ ID NO: | Type | Species | Description | Sequence |
|---|---|---|---|---|
| 18 | PRT | Artificial sequence | LCDR2 of A5 | GSINRPS |
| 19 | PRT | Artificial sequence | LCDR2 of F6 | RNINRPS |
| 20 | PRT | Artificial sequence | LCDR3 of A4, C4 and H12 | AAWDDSLSGLV |
| 21 | PRT | Artificial sequence | LCDR3 of A5 | AAWDSSSSGLV |
| 22 | PRT | Artificial sequence | LCDR3 of G4 | AAWDESITGLV |
| 23 | PRT | Artificial sequence | LCDR3 of F6 | AAWDGSLLGLV |
| 24 | PRT | Artificial sequence | LCDR3 of F9 | AAWDGTLTGLL |
| 25 | PRT | Artificial sequence | LCDR3 of B11 | AAWDGGLLGLV |
| 26 | PRT | Artificial sequence | VH of C4 | EVQLLESGGGLVQPGGSLRLSCAASGFTFSTYGMHWVRQAPGKGLEWLSYISGGSSYIFYADTVRGRFTISRDNSENALYLQMNSLRAEDTAVYYCARILRGGSGMDLWGQGTLVTVSS |
| 27 | PRT | Artificial sequence | VL of A4 and C4 | QSVLTQPPSASGTPGQRVTISCTGSTSNIGAGYKVYWYQQLPGTAPKLLIYGNINRPSGVPDRFSGSKSGTSASLAISGLRSEDEADYYCAAWDDSLSGLVFGGGTKLTVLG |
| 28 | PRT | Artificial sequence | VL of A5 | QSVLTQPPSASGTPGQRVTISCTGSSSNIGAGYHVYWYQQLPGTAPKLLIYGSINRPSGVPDRFSGSKSGTSGSLAISGLRSEDEADYYCAAWDSSSSGLVFGGGTKLTVLG |
| 29 | PRT | Artificial sequence | VL of G4 | QSVLTQPPSASGTPGQRVTISCTGSSSNIGAGYKVYWYQQLPGTAPKLLIYGNINRPSGVPDRFSGSKSGTSASLAISGLRSEDEADYYCAAWDESITGLVFGGGTKLTVLG |
| 30 | PRT | Artificial sequence | VL of F6 | QSVLTQPPSASGTPGQRVTISCTGSSSNIGAGYDVYWYQQLPGTAPKLLIYRNINRPSGVPDRFSGSKSGTSASLAISGLRSEDEADYYCAAWDGSLLGLVFGGGTKLTVLG |
| 31 | PRT | Artificial sequence | VL of F9 | QSVLTQPPSASGTPGQRVTISCTGSSSNIGAGYGVYWYQQLPGTAPKLLIYGNINRPSGVPDRFSGSKSGTSASLAISGLRSEDEADYYCAAWDGTLTGLLFGGGTKLTVLG |
| 32 | PRT | Artificial sequence | VL of H12 | QSVLTQPPSASGTPGQRVTISCTGSSSNIGAGYNVYWYQQLPGTAPKLLIYGNINRPSGVPDRFSGSKSGTSASLAISGLRSEDEADYYCAAWDDSLSGLVFGGGTKLTVLG |
| 33 | PRT | Artificial sequence | VL of B11 | QSVLTQPPSASGTPGQRVTISCTGSSSNIGAGYNVYWYQQLPGTAPKLLIYGNINRPSGVPDRFSGSKSGTSASLAISGLRSEDEADYYCAAWDGGLLGLVFGGGTKLTVLG |

| SEQ ID NO: | Type | Species | Description | Sequence |
|---|---|---|---|---|
| 34 | PRT | Artificial sequence | HCDR1 of M126 | SSSYYWG |
| 35 | PRT | Artificial sequence | HCDR2 of M126 | NIYYRGDTYYSPSLKS |
| 36 | PRT | Artificial sequence | HCDR3 of M126 | GFRFDY |
| 37 | PRT | Artificial sequence | LCDR1 of M126 | TGTSSDVGGYNYVS |
| 38 | PRT | Artificial sequence | LCDR2 of M126 | EVSKRPS |
| 39 | PRT | Artificial sequence | LCDR3 of M126 | SSYAGSNNLV |
| 40 | PRT | Artificial sequence | VH of M126 | QLQLQESGPGLVKPSETLSLTCTVSGGSISSSSYYWGWIRQPPGKGLEWIGNIYYRGDTYYSPSLKSRVTISVDTSKNQFSLKLSSVTAADTAVYYCAKGFRFDYWGQGTLVTVSS |
| 41 | PRT | Artificial sequence | VL of M126 | QSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNNLVFGGGTKLTVL |
| 42 | PRT | Artificial sequence | VH of C40M9 | QLQLQESGPGLVKPSEILSLTCTVSGGSISSSSYYWGWIRQPPGKGLEWIGNIYYRGDTYYSPSLKSRVTISVDTSKNQFSLKLNSVTAADTAVYYCAKGFRFDYWGQGTLVTVSS |
| 43 | PRT | Artificial sequence | VL of C40M9 | QSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNNLVFGGGTKLTVL |
| 44 | PRT | Artificial sequence | VH of CP-870,893 | QVQLVQSGAEVKKPGASVKVSCKASGYTFTGYYMHWVRQAPGQGLEWMGWINPDSGGTNYAQKFQGRVTMTRDTSISTAYMELNRLRSDDTAVYYCARDQPLGYCTNGVCSYFDYWGQGTLVTVSS |
| 45 | PRT | Artificial sequence | VL of CP-870,893 | DIQMTQSPSSVSASVGDRVTITCRASQGIYSWLAWYQQKPGKAPNLLIYTASTLQSGVPSRFSGSGSGTDFTLTISSLQPEDFATYYCQQANIFPLTFGGGTKVEIK |
| 46 | PRT | Artificial sequence | VH of APX-005 | QVQLVESGGGVVQPGRSLRLSCAASGFSFSSTYVCWVRQAPGKGLEWIACIYTGDGTNYSASWAKGRFTISKDSSKNTVYLQMNSLRAEDTAVYFCARPDITYGFAINFWGPGTLVTVSS |
| 47 | PRT | Artificial sequence | VL of APX-005 | DIQMTQSPSSLSASVGDRVTIKCQASQSISSRLAWYQQKPGKPPKLLIYRASTLASGVPSRFSGSGSGTDFTLTISSLQPEDVATYYCQCTGYGISWPIGGGTKVEIK |
| 48 | PRT | Artificial sequence | HC of M126 | QLQLQESGPGLVKPSETLSLTCTVSGGSISSSSYYWGWIRQPPGKGLEWIGNIYYRGDTYYSPSLKSRVTISVDTSKNQFSLKLSSVTAADTAVYYCAKGFRFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE |

| SEQ ID NO: | Type | Species | Description | Sequence |
|---|---|---|---|---|
| | | | | NNYKTTPPVLDSDGSFFLYSKLTVDKSRWQQG NVFSCSVMHEALHNHYTQKSLSLSPGK |
| 49 | PRT | Artificial sequence | LC of M126 | QSALTQPPSASGSPGQSVTISCTGTSSDV GGYNYVSWYQQHPGKAPKLMIYEVSKRPS GVPDRFSGSKSGNTASLTVSGLQAEDEAD YYCSSYAGSNNLVFGGGTKLTVLGQPKAA PSVTLFPPSSEELQANKATLVCLISDFYP GAVTVAWKADSSPVKAGVETTTPSKQSNN KYAASSYLSLTPEQWKSHRSYSCQVTHEG STVEKTVAPTECS |

We claim:

1. A method of treating a cancer comprising administering to a subject in need thereof a therapeutically effective amount of a co-therapy comprising
(a) a compound of formula (I)

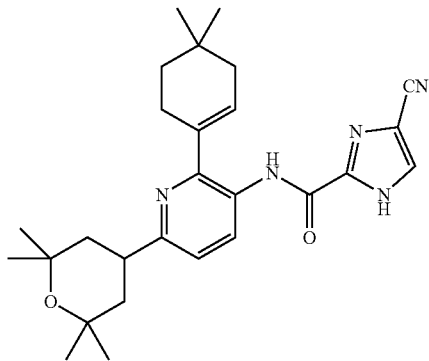

(I)

or a solvate, hydrate, tautomer, or pharmaceutically acceptable salt thereof and
(b) an agonistic antibody or an antigen-binding fragment thereof that specifically binds CD40;
wherein said agonistic antibody or an antigen-binding fragment thereof comprises a heavy chain variable region 1 (HCDR1), a HCDR2, a HCDR3, a light chain complementarity determining region 1 (LCDR1), a LCDR2 and a LCDR3 of SEQ ID NOs: 2, 3, 4, 5, 6 and 7, respectively, and a heavy chain variable region (VH) and a light chain variable region (VL) of SEQ ID NOs: 8 and 9, respectively; and
wherein said subject is resistant or refractory to treatment with a CSF-1R inhibitor, or is resistant or refractory to treatment with a CD40 agonist.

2. The method of claim 1, wherein the cancer is a solid tumor or a hematological malignancy.

3. The method of claim 1, wherein the cancer is selected from the group consisting of pancreatic cancer, prostate cancer, colorectal cancer, lung cancer, non-Hodgkin's lymphoma, breast cancer and melanoma.

4. The method of claim 1, wherein the cancer is selected from the group consisting of pancreatic cancer, prostate cancer, colorectal cancer and non-small cell lung cancer.

5. The method of claim 3, wherein the prostate cancer is castration resistant prostate cancer.

6. The method of claim 3, wherein the lung cancer is non-small cell lung cancer (NSCLC).

7. The method of claim 1, wherein the subject is resistant or refractory to treatment with a CSF-1R inhibitor.

8. The method of claim 1 wherein the subject is resistant or refractory to treatment with a CD40 agonist.

9. The method of claim 1, wherein the compound of formula (I) and the agonistic antibody or the antigen-binding fragment thereof that specifically binds CD40 are administered concurrently, sequentially or separately.

10. The method of claim 1, wherein the compound of formula (I) is administered prior to administration of the agonistic antibody or the antigen-binding fragment thereof that specifically binds CD40 or wherein the compound of formula (I) is administered prior to and then concurrently with administration of the agonistic antibody or the antigen-binding fragment thereof that specifically binds CD40.

11. The method of claim 1, further comprising administering to the subject radiation therapy or at least one additional cancer therapeutic agent.

12. The method of claim 11, wherein the at least one additional cancer therapeutic agent is a standard of care drug for treatment of the cancer.

13. The method of claim 10, wherein the compound of formula (I) is administered prior to administration of the agonistic antibody or the antigen-binding fragment thereof that specifically binds CD40.

14. The method of claim 13, wherein the compound of formula (I) is administered daily for between 1 and 30 days prior to administration of the agonistic antibody or the antigen-binding fragment thereof that specifically binds CD40.

15. The method of claim 13, wherein the compound of formula (I) is administered daily for between 7 and 14 days prior to administration of the agonistic antibody or the antigen-binding fragment thereof that specifically binds CD40.

16. The method of claim 10, wherein the compound of formula (I) is administered in an amount in the range of from about 10 mg per day to about 600 mg per day.

17. The method of claim 10, wherein the compound of formula (I) is administered in an amount in the range of from about 50 mg per day to about 300 mg per day.

18. The method of claim 10, wherein the compound of formula (I) is administered in an amount in the range of from about 100 mg per day to about 200 mg per day.

19. The method of claim 10, wherein the compound of formula (I) is administered daily for between 7 and 14 days prior to administration of the agonistic antibody or the antigen-binding fragment thereof that specifically binds CD40, and then further administered concurrently with administration of the agonistic antibody or the antigen-binding fragment thereof that specifically binds CD40.

20. The method of claim 10, wherein the agonistic antibody or the antigen-binding fragment thereof that specifically binds CD40 is administered between about once a week and about once every three months, in an amount in the range of from about 1 mg/kg to about 100 mg/kg.

21. The method of claim 10, wherein the agonistic antibody or the antigen-binding fragment thereof that specifically binds CD40 is administered once a week or once a month in an amount in the range of from about 1 mg/kg to about 50 mg/kg.

22. The method of claim 1, wherein the agonistic antibody or the antigen-binding fragment thereof binds CD40 within CD40 residues 24-59 of SEQ ID NO: 1.

23. The method of claim 1, wherein the antibody is an IgG1, an IgG2, an IgG3 or an IgG4 isotype.

24. The method of claim 23, wherein the antibody comprises at least one mutation in an Fc region.

25. The method of claim 24, wherein the at least one mutation enhances binding of the antibody to FcγRIIb.

26. The method of claim 25, wherein the at least one mutation in the Fc region is a S267E mutation, a S267E/I332E mutation, a S267E/L328F mutation, a G236D/S267E mutation or a E233D/G237D/H268D/P271G/A330R/P238D mutation, residue numbering according to the EU Index.

27. A method of treating a cancer comprising administering to a subject in need thereof a therapeutically effective amount of a co-therapy comprising
(a) a compound of formula (I)

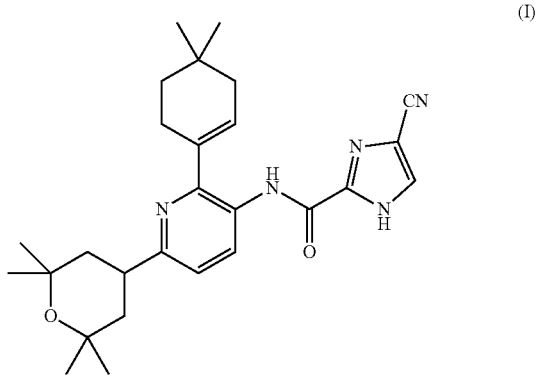 [SMILES: CC1(C)CC=C(c2nc(C3CC(C)(C)OC(C)(C)C3)ccc2NC(=O)c2nc(C#N)c[nH]2)CC1]

(I)

or a solvate, hydrate, tautomer, or pharmaceutically acceptable salt thereof and
(b) an agonistic antibody or an antigen-binding fragment thereof that specifically binds CD40;
wherein said agonistic antibody or an antigen-binding fragment thereof comprises a heavy chain variable region 1 (HCDR1), a HCDR2, a HCDR3, a light chain complementarity determining region 1 (LCDR1), a LCDR2 and a LCDR3 of SEQ ID NOs: 2, 3, 4, 5, 6 and 7, respectively, and a heavy chain variable region (VH) and a light chain variable region (VL) of SEQ ID NOs: 8 and 9, respectively; and
wherein said cancer is castration resistant prostate cancer.

28. The method of claim 27, wherein the subject is resistant or refractory to treatment with a CSF-1R inhibitor.

29. The method of claim 27 wherein the subject is resistant or refractory to treatment with a CD40 agonist.

30. The method of claim 27, wherein the compound of formula (I) and the agonistic antibody or the antigen-binding fragment thereof that specifically binds CD40 are administered concurrently, sequentially or separately.

31. The method of claim 27, wherein the compound of formula (I) is administered prior to administration of the agonistic antibody or the antigen-binding fragment thereof that specifically binds CD40 or wherein the compound of formula (I) is administered prior to and then concurrently with administration of the agonistic antibody or the antigen-binding fragment thereof that specifically binds CD40.

32. The method of claim 27, further comprising administering to the subject radiation therapy or at least one additional cancer therapeutic agent.

33. The method of claim 32, wherein the at least one additional cancer therapeutic agent is a standard of care drug for treatment of the cancer.

34. The method of claim 31, wherein the compound of formula (I) is administered prior to administration of the agonistic antibody or the antigen-binding fragment thereof that specifically binds CD40.

35. The method of claim 34, wherein the compound of formula (I) is administered daily for between 1 and 30 days prior to administration of the agonistic antibody or the antigen-binding fragment thereof that specifically binds CD40.

36. The method of claim 34, wherein the compound of formula (I) is administered daily for between 7 and 14 days prior to administration of the agonistic antibody or the antigen-binding fragment thereof that specifically binds CD40.

37. The method of claim 31, wherein the compound of formula (I) is administered in an amount in the range of from about 10 mg per day to about 600 mg per day.

38. The method of claim 31, wherein the compound of formula (I) is administered in an amount in the range of from about 50 mg per day to about 300 mg per day.

39. The method of claim 31, wherein the compound of formula (I) is administered in an amount in the range of from about 100 mg per day to about 200 mg per day.

40. The method of claim 31, wherein the compound of formula (I) is administered daily for between 7 and 14 days prior to administration of the agonistic antibody or the antigen-binding fragment thereof that specifically binds CD40, and then further administered concurrently with administration of the agonistic antibody or the antigen-binding fragment thereof that specifically binds CD40.

41. The method of claim 31, wherein the agonistic antibody or the antigen-binding fragment thereof that specifically binds CD40 is administered between about once a week and about once every three months, in an amount in the range of from about 1 mg/kg to about 100 mg/kg.

42. The method of claim 27, wherein the agonistic antibody or the antigen-binding fragment thereof that specifically binds CD40 is administered once a week or once a month in an amount in the range of from about 1 mg/kg to about 50 mg/kg.

43. The method of claim 27, wherein the agonistic antibody or the antigen-binding fragment thereof binds CD40 within CD40 residues 24-59 of SEQ ID NO: 1.

44. The method of claim 27, wherein the antibody is an IgG1, an IgG2, an IgG3 or an IgG4 isotype.

45. The method of claim 44, wherein the antibody comprises at least one mutation in an Fc region.

46. The method of claim 45, wherein the at least one mutation enhances binding of the antibody to FcγRIIb.

47. The method of claim 45, wherein the at least one mutation in the Fc region is a S267E mutation, a S267E/I332E mutation, a S267E/L328F mutation, a G236D/S267E mutation or a E233D/G237D/H268D/P271G/A330R/P238D mutation, residue numbering according to the EU Index.

* * * * *

SEQUENCE LISTING

<160> NUMBER OF SEQ ID NOS: 49

<210> SEQ ID NO 1
<211> LENGTH: 277
<212> TYPE: PRT
<213> ORGANISM: Homo sapiens

<400> SEQUENCE: 1

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255
```

```
Gly Cys Gln Pro Val Thr Gln Glu Asp Gly Lys Glu Ser Arg Ile Ser
            260                 265                 270

Val Gln Glu Arg Gln
        275

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      HCDR1 of ADC-1013, A4, A5, C4, G4, F6, F9, H12, B11

<400> SEQUENCE: 2

Thr Tyr Gly Met His
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      HCDR2 of ADC-1013, A4, A5, G4, F6, F9, H12, B11

<400> SEQUENCE: 3

Tyr Ile Ser Gly Gly Ser Ser Tyr Ile Phe Tyr Ala Asp Ser Val Arg
1               5                   10                  15

Gly

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      HCDR3 of ADC-1013, A4, A5, C4, G4, F6, F9, H12, B11

<400> SEQUENCE: 4

Ile Leu Arg Gly Gly Ser Gly Met Asp Leu
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      LCDR1 of ADC-1013, H12 and B11

<400> SEQUENCE: 5

Thr Gly Ser Ser Ser Asn Ile Gly Ala Gly Tyr Asn Val Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      LCDR2 of ADC-1013, A4, C4, G4, F9, H12 and B11

<400> SEQUENCE: 6

Gly Asn Ile Asn Arg Pro Ser
1               5
```

```
<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR3 of ADC-1013

<400> SEQUENCE: 7

Ala Ala Trp Asp Lys Ser Ile Ser Gly Leu Val
1               5                   10

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      VH of ADC-1013, A4, A5, G4, F6, F9, H12 and B11

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      VL of ADC-1013

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asn Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Lys Ser
                85                  90                  95

Ile Ser Gly Leu Val Phe Gly Gly Gly Thr Lys Leu Thr Val Leu Gly
```

<210> SEQ ID NO 10
<211> LENGTH: 449
<212> TYPE: PRT
<213> ORGANISM: Artificial Sequence
<220> FEATURE:
<223> OTHER INFORMATION: Description of Artificial Sequence: Synthetic HC of ADC-1013

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 11
<211> LENGTH: 217
<212> TYPE: PRT
<213> ORGANISM: Artificial Sequence
<220> FEATURE:
<223> OTHER INFORMATION: Description of Artificial Sequence: Synthetic
      LC of ADC-1013

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asn Val Tyr Trp Tyr Gln Gln Leu Pro Gly Thr Ala Pro Lys Leu
            35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Lys Ser
                85                  90                  95

Ile Ser Gly Leu Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 12
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      HCDR2 of C4

<400> SEQUENCE: 12

Tyr Ile Ser Gly Gly Ser Ser Tyr Ile Phe Tyr Ala Asp Thr Val Arg
1               5                   10                  15

Gly

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      LCDR1 fo A4 and C4

<400> SEQUENCE: 13

Thr Gly Ser Thr Ser Asn Ile Gly Ala Gly Tyr Lys Val Tyr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Gly Ser Ser Ser Asn Ile Gly Ala Gly Tyr His Val Tyr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      LCDR1 of G4

<400> SEQUENCE: 15

Thr Gly Ser Ser Ser Asn Ile Gly Ala Gly Tyr Lys Val Tyr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      LCDR1 of F6

<400> SEQUENCE: 16

Thr Gly Ser Ser Ser Asn Ile Gly Ala Gly Tyr Asp Val Tyr
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      LCDR1 of F9

<400> SEQUENCE: 17

Thr Gly Ser Ser Ser Asn Ile Gly Ala Gly Tyr Gly Val Tyr
1               5                   10
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      LCDR2 of A5

<400> SEQUENCE: 18

Gly Ser Ile Asn Arg Pro Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      LCDR2 of F6

<400> SEQUENCE: 19

Arg Asn Ile Asn Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR3 of A4, C4 and H12

<400> SEQUENCE: 20

Ala Ala Trp Asp Asp Ser Leu Ser Gly Leu Val
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR3 of A5

<400> SEQUENCE: 21

Ala Ala Trp Asp Ser Ser Ser Ser Gly Leu Val
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR3 of G4

<400> SEQUENCE: 22

Ala Ala Trp Asp Glu Ser Ile Thr Gly Leu Val
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR3 of F6

```
<400> SEQUENCE: 23

Ala Ala Trp Asp Gly Ser Leu Leu Gly Leu Val
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR3 of F9

<400> SEQUENCE: 24

Ala Ala Trp Asp Gly Thr Leu Thr Gly Leu Leu
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR3 of B11

<400> SEQUENCE: 25

Ala Ala Trp Asp Gly Gly Leu Leu Gly Leu Val
1               5                   10

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      VH of C4

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Thr Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: Synthetic
      VL of A4 and C4

<400> SEQUENCE: 27
```

Gln Ser Val Leu Thr Gln Pro Pro Ser Ala Ser Gly Thr Pro Gly Gln
1               5                   10                  15

Arg Val Thr Ile Ser Cys Thr Gly Ser Thr Ser Asn Ile Gly Ala Gly
                20                  25                  30

Tyr Lys Val Tyr Trp Tyr Gln Gln Leu Pro Gly Thr Ala Pro Lys Leu
            35                  40                  45

Leu Ile Tyr Gly Asn Ile Asn Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Leu Val Phe Gly Gly Gly Thr Lys Leu Thr Val Leu Gly
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      VL of A5

<400> SEQUENCE: 28

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr His Val Tyr Trp Tyr Gln Gln Leu Pro Gly Thr Ala Pro Lys Leu
            35                  40                  45

Leu Ile Tyr Gly Ser Ile Asn Arg Pro Ser Gly Val Pro Asp Arg Phe
        50                  55                  60

Ser Gly Ser Lys Ser Gly Thr Ser Gly Ser Leu Ala Ile Ser Gly Leu
65                  70                  75                  80

Arg Ser Glu Asp Glu Ala Asp Tyr Tyr Cys Ala Ala Trp Asp Ser Ser
                85                  90                  95

Ser Ser Gly Leu Val Phe Gly Gly Gly Thr Lys Leu Thr Val Leu Gly
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic
      VL of G4

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Lys Val Tyr Trp Tyr Gln Gln Leu Pro Gly Thr Ala Pro Lys Leu
            35                  40                  45

Leu Ile Tyr Gly Asn Ile Asn Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

```
Arg Ser Glu Asp Glu Ala Asp Tyr Tyr Cys Ala Ala Trp Asp Glu Ser
                85                  90                  95

Ile Thr Gly Leu Val Phe Gly Gly Gly Thr Lys Leu Thr Val Leu Gly
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      VL of F6

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Arg Asn Ile Asn Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Gly Ser
                85                  90                  95

Leu Leu Gly Leu Val Phe Gly Gly Gly Thr Lys Leu Thr Val Leu Gly
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      VL of F9

<400> SEQUENCE: 31

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Gly Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Gly Thr
                85                  90                  95

Leu Thr Gly Leu Leu Phe Gly Gly Gly Thr Lys Leu Thr Val Leu Gly
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      VL of H12
```

<400> SEQUENCE: 32

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asn Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Leu Val Phe Gly Gly Gly Thr Lys Leu Thr Val Leu Gly
            100                 105                 110
```

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      VL of B11

<400> SEQUENCE: 33

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asn Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Gly Gly
                85                  90                  95

Leu Leu Gly Leu Val Phe Gly Gly Gly Thr Lys Leu Thr Val Leu Gly
            100                 105                 110
```

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      HCDR1 of M126

<400> SEQUENCE: 34

```
Ser Ser Ser Tyr Tyr Trp Gly
1               5
```

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      HCDR2 of M126

```
<400> SEQUENCE: 35

Asn Ile Tyr Tyr Arg Gly Asp Thr Tyr Tyr Ser Pro Ser Leu Lys Ser
1               5                   10                  15

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      HCDR3 of M126

<400> SEQUENCE: 36

Gly Phe Arg Phe Asp Tyr
1               5

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      LCDR1 of M126

<400> SEQUENCE: 37

Thr Gly Thr Ser Ser Asp Val Gly Gly Tyr Asn Tyr Val Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      LCDR2 of M126

<400> SEQUENCE: 38

Glu Val Ser Lys Arg Pro Ser
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      LCDR3 of M126

<400> SEQUENCE: 39

Ser Ser Tyr Ala Gly Ser Asn Asn Leu Val
1               5                   10

<210> SEQ ID NO 40
<211> LENGTH: 116
<212> TYPE: PRT
<213> ORGANISM: Artificial Sequence
<220> FEATURE:
<223> OTHER INFORMATION: Description of Artificial Sequence: Synthetic
      VH of M126

<400> SEQUENCE: 40

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
```

```
            35                  40                  45

Trp Ile Gly Asn Ile Tyr Tyr Arg Gly Asp Thr Tyr Tyr Ser Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Lys Gly Phe Arg Phe Asp Tyr Trp Gly Gln Gly Thr Leu Val
                100                 105                 110

Thr Val Ser Ser
            115

<210> SEQ ID NO 41
<211> LENGTH: 110
<212> TYPE: PRT
<213> ORGANISM: Artificial Sequence
<220> FEATURE:
<223> OTHER INFORMATION: Description of Artificial Sequence: Synthetic
      VL of M126

<400> SEQUENCE: 41

Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
     50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Leu Val Phe Gly Gly Gly Thr Lys Leu Thr Val Leu
                100                 105                 110

<210> SEQ ID NO 42
<211> LENGTH: 116
<212> TYPE: PRT
<213> ORGANISM: Artificial Sequence
<220> FEATURE:
<223> OTHER INFORMATION: Description of Artificial Sequence: Synthetic
      VH of C40M9

<400> SEQUENCE: 42

Gln Leu Gln Leu Gln Glu Ser Gly Pro Gly Leu Val Lys Pro Ser Glu
 1               5                  10                  15

Ile Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Arg Gly Asp Thr Tyr Tyr Ser Pro Ser
     50                  55                  60

Leu Lys Ser Arg Val Thr Ile Ser Val Asp Thr Ser Lys Asn Gln Phe
 65                  70                  75                  80

Ser Leu Lys Leu Asn Ser Val Thr Ala Ala Asp Thr Ala Val Tyr Tyr
                 85                  90                  95

Cys Ala Lys Gly Phe Arg Phe Asp Tyr Trp Gly Gln Gly Thr Leu Val
```

-continued

```
                100                 105                 110

Thr Val Ser Ser
        115

<210> SEQ ID NO 43
<211> LENGTH: 110
<212> TYPE: PRT
<213> ORGANISM: Artificial Sequence
<220> FEATURE:
<223> OTHER INFORMATION: Description of Artificial Sequence: Synthetic
      VL of C40M9

<400> SEQUENCE: 43

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu
            100                 105                 110

<210> SEQ ID NO 44
<211> LENGTH: 126
<212> TYPE: PRT
<213> ORGANISM: Artificial Sequence
<220> FEATURE:
<223> OTHER INFORMATION: Description of Artificial Sequence: Synthetic
      VH of CP-870,893

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser
        115                 120                 125

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
```

-continued

VL of CP-870,893

<400> SEQUENCE: 45

Asp Ile Gln Met Thr Gln Ser Pro Ser Ser Val Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys
            100                 105

<210> SEQ ID NO 46
<211> LENGTH: 120
<212> TYPE: PRT
<213> ORGANISM: Artificial Sequence
<220> FEATURE:
<223> OTHER INFORMATION: Description of Artificial Sequence: Synthetic
      VH of APX-005

<400> SEQUENCE: 46

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Thr
            20                  25                  30

Tyr Val Cys Trp Val Arg Gln Ala Pro Gly Lys Gly Leu Glu Trp Ile
        35                  40                  45

Ala Cys Ile Tyr Thr Gly Asp Gly Thr Asn Tyr Ser Ala Ser Trp Ala
    50                  55                  60

Lys Gly Arg Phe Thr Ile Ser Lys Asp Ser Ser Lys Asn Thr Val Tyr
65                  70                  75                  80

Leu Gln Met Asn Ser Leu Arg Ala Glu Asp Thr Ala Val Tyr Phe Cys
                85                  90                  95

Ala Arg Pro Asp Ile Thr Tyr Gly Phe Ala Ile Asn Phe Trp Gly Pro
            100                 105                 110

Gly Thr Leu Val Thr Val Ser Ser
        115                 120

<210> SEQ ID NO 47
<211> LENGTH: 108
<212> TYPE: PRT
<213> ORGANISM: Artificial Sequence
<220> FEATURE:
<223> OTHER INFORMATION: Description of Artificial Sequence: Synthetic
      VL of APX-005

<400> SEQUENCE: 47

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Ser Ser Arg
            20                  25                  30

Leu Ala Trp Tyr Gln Gln Lys Pro Gly Lys Pro Pro Lys Leu Leu Ile
        35                  40                  45

```
Tyr Arg Ala Ser Thr Leu Ala Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Cys Thr Gly Tyr Gly Ile Ser
                 85                  90                  95

Trp Pro Ile Gly Gly Gly Thr Lys Val Glu Ile Lys
            100                 105
```

<210> SEQ ID NO 48
<211> LENGTH: 446
<212> TYPE: PRT
<213> ORGANISM: Artificial Sequence
<220> FEATURE:
<223> OTHER INFORMATION: Description of Artificial Sequence: Synthetic HC of M126

<400> SEQUENCE: 48

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
         35                  40                  45

Trp Ile Gly Asn Ile Tyr Tyr Arg Gly Asp Thr Tyr Tyr Ser Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Lys Gly Phe Arg Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
```

```
                    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                    325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 49
<211> LENGTH: 216
<212> TYPE: PRT
<213> ORGANISM: Artificial Sequence
<220> FEATURE:
<223> OTHER INFORMATION: Description of Artificial Sequence: Synthetic
      LC M126

<400> SEQUENCE: 49

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190
```

```
Arg Ser Tyr Ser Cys Gln Val Thr His Glu Gly Ser Thr Val Glu Lys
        195                 200                 205
Thr Val Ala Pro Thr Glu Cys Ser
    210                 215
```